(12) United States Patent
Hayashizaki et al.

(10) Patent No.: US 10,294,261 B2
(45) Date of Patent: *May 21, 2019

(54) COMPOUND, NUCLEIC ACID, LABELING SUBSTANCE, AND DETECTION METHOD

(71) Applicant: KABUSHIKI KAISHA DNAFORM, Yokohama-shi, Kanagawa (JP)

(72) Inventors: Yoshihide Hayashizaki, Tsukuba (JP); Takahiro Soma, Tokyo (JP); Takeshi Hanami, Yokohama (JP); Hajime Kanamori, Ageo (JP); Masaru Baba, Yokohama (JP)

(73) Assignee: KABUSHIKI KAISHA DNAFORM, Kanagawa (JP)

( * ) Notice: Subject to any disclaimer, the term of this patent is extended or adjusted under 35 U.S.C. 154(b) by 128 days.

This patent is subject to a terminal disclaimer.

(21) Appl. No.: 14/424,826

(22) PCT Filed: Sep. 3, 2013

(86) PCT No.: PCT/JP2013/073721

§ 371 (c)(1),
(2) Date: Feb. 27, 2015

(87) PCT Pub. No.: WO2014/038561

PCT Pub. Date: Mar. 13, 2014

(65) Prior Publication Data

US 2015/0252070 A1 Sep. 10, 2015

(30) Foreign Application Priority Data

Sep. 4, 2012 (JP) .................................. 2012-193727

(51) Int. Cl.
*C07H 19/06* (2006.01)
*C07H 21/04* (2006.01)
(Continued)

(52) U.S. Cl.
CPC ........... *C07H 19/06* (2013.01); *C07H 19/073* (2013.01); *C07H 21/04* (2013.01); *C09B 23/04* (2013.01);
(Continued)

(58) Field of Classification Search
CPC ...... C07H 19/073; C07H 19/06; C07H 21/04; Y02P 20/55; C12Q 1/6876
See application file for complete search history.

(56) References Cited

U.S. PATENT DOCUMENTS

| 4,415,732 | A | * | 11/1983 | Caruthers | ............... | C07H 21/00 |
| | | | | | | 536/26.5 |
| 4,668,777 | A | * | 5/1987 | Caruthers | ............... | C07H 21/00 |
| | | | | | | 536/26.5 |

(Continued)

FOREIGN PATENT DOCUMENTS

| JP | 2002-507203 | 3/2002 |
| JP | 2006-047183 | 2/2006 |

(Continued)

OTHER PUBLICATIONS

Ikeda et al., "Doubly Thiazole Orange-Labeled Cytidine for Functional Expansion for a Hybridization-Sensitive Probe," Tetrahedron Letters, 50(51), 7191-7195 (2009).*

(Continued)

*Primary Examiner* — Lawrence E Crane
(74) *Attorney, Agent, or Firm* — Hamre, Schumann, Mueller & Larson, P.C.

(57) ABSTRACT

The present invention provides a compound represented by the following chemical formula (I); a tautomer or stereoisomer of the compound; or a salt of the compound, the tautomer, or the stereoisomer.

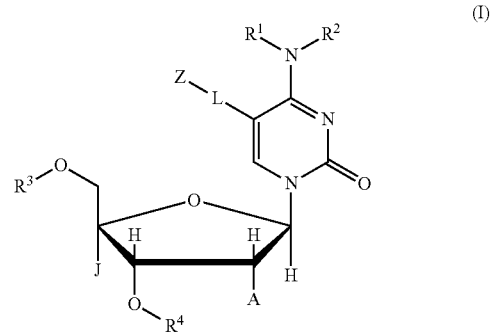

In the chemical formula (I), $R^1$ and $R^2$ are each a Group 1 element or a protecting group of an amino group and may be identical to or different from each other, or alternatively, $R^1$ and $R^2$ together may form a protecting group of an amino group. $R^3$ is a Group 1 element or a protecting group of a hydroxy group. $R^4$ is a Group 1 element or $-PR^5R^6R^7R^8$ ($R^5$, $R^6$, $R^7$, and $R^8$ are each a Group 1 element, a lone electron pair, a Group 16 element, a Group 17 element, or a protecting group of a phosphorus atom, and may be identical to or different from each other). J is a hydrogen atom or an arbitrary atomic group, A is a hydrogen atom, a hydroxy group, an alkyl group, an aralkyl group, an alkoxy group, an electron-withdrawing group, a silylene group, or a sulfide group, or alternatively, J and A together may form a linker. L is a single bond or a linker (a linking atom or a linking atomic group), the main chain length (the number of main chain atoms) of the linker is arbitrary, L may or may not contain each of C, N, O, S, P, and Si in the main chain, and may or may not contain each of a single bond, a double bond, a triple bond, an amide bond, an ester bond, a disulfide bond, an imino group, an ether bond, a thioether bond, and a thioester bond in the main chain. Z is an atomic group that can form a peptide bond with a labeling compound, or is an atom or atomic group including a label.

18 Claims, 1 Drawing Sheet

Specification includes a Sequence Listing.

(51) Int. Cl.
    *C09B 23/04*     (2006.01)
    *C09B 23/06*     (2006.01)
    *C07H 19/073*     (2006.01)
    *C12Q 1/6876*     (2018.01)

(52) U.S. Cl.
    CPC ............ *C09B 23/06* (2013.01); *C12Q 1/6876* (2013.01); *Y02P 20/55* (2015.11)

(56) References Cited

U.S. PATENT DOCUMENTS

| | | | |
|---|---|---|---|
| 4,973,679 A * | 11/1990 | Caruthers | C07H 21/00 536/25.3 |
| 5,132,418 A * | 7/1992 | Caruthers | B01J 19/0046 536/25.3 |
| 5,986,086 A | 11/1999 | Brush et al. | |
| 8,536,323 B2 * | 9/2013 | Opperman | C07H 19/10 536/26.3 |
| 9,206,216 B2 * | 12/2015 | Etienne | C07H 19/10 |
| 2007/0190531 A1 | 8/2007 | Mitani et al. | |
| 2008/0227104 A1 | 9/2008 | Hayashizaki et al. | |
| 2011/0262917 A1 | 10/2011 | Opperman et al. | |
| 2013/0122506 A1 | 5/2013 | Hirao et al. | |
| 2013/0289263 A1 | 10/2013 | Okamoto et al. | |

FOREIGN PATENT DOCUMENTS

| | | |
|---|---|---|
| JP | 3897805 B2 | 3/2007 |
| JP | 2008-526877 | 7/2008 |
| JP | 4370385 B2 | 11/2009 |
| WO | 2006/074351 | 7/2006 |
| WO | 2007/111324 | 10/2007 |
| WO | 2008/111485 | 9/2008 |
| WO | 2011/132801 | 10/2011 |
| WO | 2012/091091 | 7/2012 |

OTHER PUBLICATIONS ( R ) Ikeda et al., "Doubly Thiazole Orange-Labeled Cytidine for Functional Expansion for a Hybridization-Sensitive Probe," Tetrahedron Letters, 50(51), 7191-7195 (2009).*

Balintová, et al., "Synthesis of nucleosides and nucleoside triphosphates bearing anthraquinone substituents as redox probes and their enzymatic incorporation to DNA", Collection Symposium Series, vol. 12, pp. 297-299, 2011.
Ikonen, et al., "Synthesis of nucleoside and nucleotide conjugates of bile acids, and polymerase construction of bile acid-functionalized DNA", Organic & Biomolecular Chemistry, vol. 8, No. 5, pp. 1194-1201, 2010.
Toenges, et al., "Note Reversed-phase liquid chromatography of biotin-labelled nucleotides a new class of markers in molecular biology", Journal of Chromatography, vol. 330, pp. 429-435, 1985.
Supplementary European Search Report for the corresponding European Patent Application No. 13834990.7, dated May 3, 2016, 14 pages.
Glen research, Cat. No. 10-1535-90, 10-1535-02.
Greene et al., "Protective groups in organic Synthesis", A Wileyinterscience publication, 1999.
Ikeda et al., "Doubly thiazole orange-labeled cytidine for functional expansion of a hybridization-sensitive probe", Tetrahedron Letters, vol. 50, Iss. 51, pp. 7191-7195, 2009.
Rye et al., "High-sensitivity two-color detection of double-stranded DNA with a confocal fluorescence gel scanner using ethidium homodimer and thiazole orange", Nucleic Acids Research, vol. 19, No. 2, pp. 327-333, 1991.
Lee et al., "Thiazole Orange: A New Dye for Reticulocyte Analysis", Cytometry, vol. 7, pp. 508-517, 1986.
Mitani et al., "Rapid SNP diagnostics using asymmetric isothermal amplification and a new mismatch-suppression technology", Nature Methods, vol. 4, No. 3, pp. 257-262, 2007.
Okamoto, "Excitonic Interaction: Another Photophysical Process for Fluorescence-Controlled Nucleic Acid Sensing", The Chemical Record, vol. 10, pp. 188-196, 2010.
Ikeda et al., "Novel fluorescent probes for detection of nucleic acids", Abstracts of Annual Meeting on Photochemistry, p. 182, 1P104, 2007.
Ikeda et al., "pH-dependent fluorescence of uncharged benzothiazolebased dyes binding to DNA", Photochemical & Photobiological Sciences, vol. 6, No. 11, pp. 1197-1201, 2007.
Office Action issued in corresponding Eurasian Patent Application No. 201590501, dated Feb. 3, 2017, 8 pages with an English translation.
IUPAC>Gold Book>Alphabetical Index>A>allcyl groups, IUPAC Gold Book, http://goldbook.iupac.org/A00228.html, Oct. 2008.

* cited by examiner

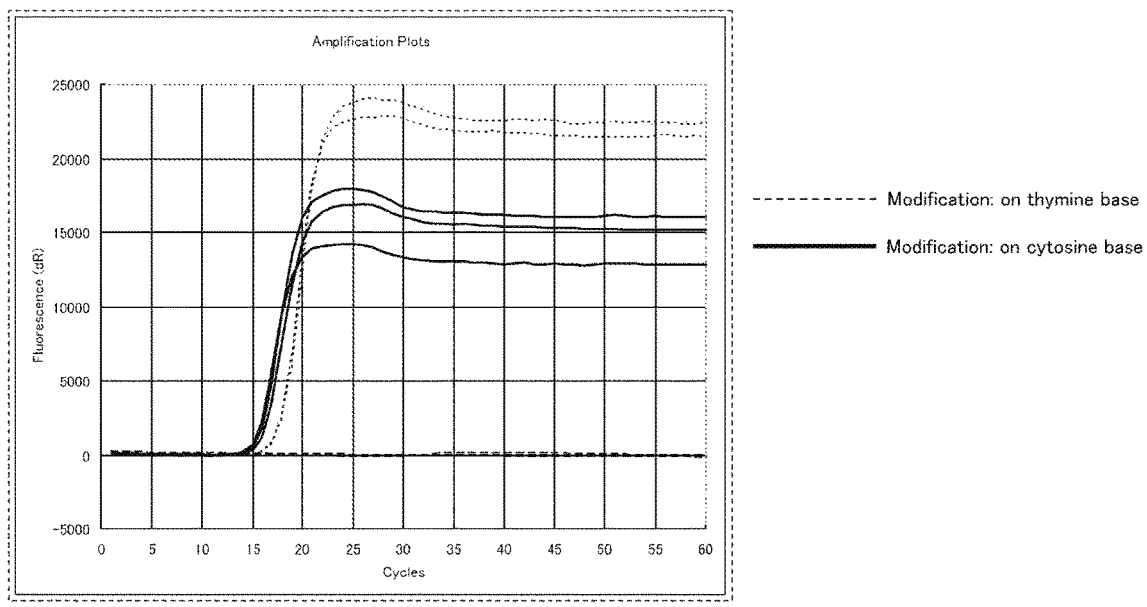

COMPOUND, NUCLEIC ACID, LABELING SUBSTANCE, AND DETECTION METHOD

CROSS-REFERENCE TO RELATED APPLICATIONS

This application is a National Stage Entry of PCT/JP2013/073721, which is based on JP2012-193727 filed Sep. 4, 2012.

TECHNICAL FIELD

The present invention relates to a compound, a nucleic acid, a labeling substance, and a detection method.

BACKGROUND ART

Analysis of biological phenomena on the cell level and diagnosis of diseases on the molecular level require the detection of a specific nucleic acid sequence. To this end, a modified DNA oligomer having a functional molecule, such as a fluorescent dye or a biologically active substance, introduced thereto is used in various experiments.

In chemical modification of a DNA oligomer, a reactive site for modification is introduced to an end or a base of the nucleic acid.

In particular, if a reactive site can be introduced to a base of a nucleic acid, it becomes possible to introduce different functional molecules to an end and the base of the nucleic acid, respectively.

It is relatively easy to introduce a reactive site to an end of a nucleic acid. However, in light of the complexity of the synthesis of a nucleic acid base etc., when a modified DNA oligomer is synthesized by introducing a functional molecule to a nucleic acid base, it is general practice to introduce the functional molecule to a thymine base having an active site.

A method used widely for this purpose is to introduce an NHS (N-hydroxysuccinimide) group as an active site, and then introduce a functional molecule through a reaction with amine. Thus, a thymine base, which has no amino group, is suitable for the introduction of a functional molecule because a side reaction is less likely to occur (Non-Patent Document 1).

CITATION LIST

Non-Patent Document(s)

[Non-Patent Document 1] Glen Research, Cat. No. 10-1535-90, 10-1535-02

DISCLOSURE OF INVENTION

Problem to be Solved by the Invention

Modification to a thymine base is carried out in many studies. However, owing to the fact that modification to other nucleic acid bases is difficult, considerable restrictions are imposed on the design of modified DNA oligomers.

Thus, in order to alleviate the restrictions on the sequence design of modified nucleic acid oligomers, it is an object of the present invention to provide a compound that is other than thymine derivatives and can be used as a reagent for synthesizing nucleic acids. The present invention also provides a nucleic acid and labeling substance that can be produced using the compound, and a detection method using the labeling substance.

Means for Solving Problem

In order to achieve the above object, the present invention provides a compound represented by the following chemical formula (I); a tautomer or stereoisomer of the compound; or a salt of the compound, the tautomer, or the stereoisomer:

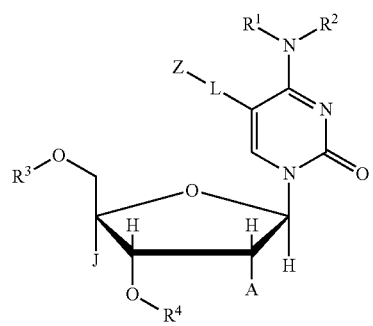

(I)

where in the chemical formula (I), $R^1$ and $R^2$ are each a Group 1 element or a protecting group of an amino group and may be identical to or different from each other, or alternatively, $R^1$ and $R^2$ together may form a protecting group of an amino group, $R^3$ is a Group 1 element or a protecting group of a hydroxy group, $R^4$ is a Group 1 element or $-PR^5R^6R^7R^8$ ($R^5$, $R^6$, $R^7$, and $R^8$ are each a Group 1 element, a lone electron pair, a Group 16 element, a Group 17 element, or a protecting group of a phosphorus atom, and may be identical to or different from each other), J is a hydrogen atom or an arbitrary atomic group, A is a hydrogen atom, a hydroxy group, an alkyl group, an aralkyl group, an alkoxy group, an electron-withdrawing group, a silylene group, or a sulfide group, or alternatively, J and A together may form a linker, L is a single bond or a linker (a linking atom or a linking atomic group), the main chain length (the number of main chain atoms) of the linker is arbitrary, L may or may not contain each of C, N, O, S, P, and Si in the main chain, and may or may not contain each of a single bond, a double bond, a triple bond, an amide bond, an ester bond, a disulfide bond, an imino group, an ether bond, a thioether bond, and a thioester bond in the main chain, and Z is an atomic group that can form a peptide bond with a labeling compound, or is an atom or atomic group including a label.

The present invention also provides a nucleic acid including at least one structure represented by the following chemical formula (II):

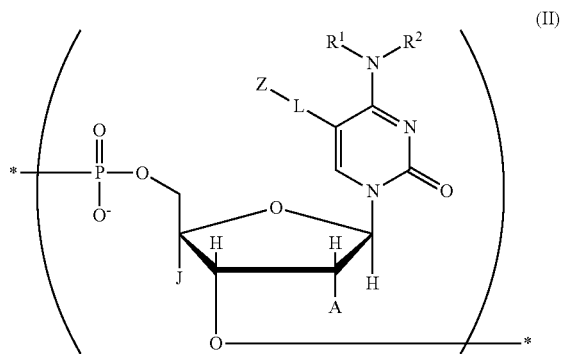

(II)

where in the chemical formula (II), $R^1$, $R^2$, J, A, L, and Z are identical to those in the above chemical formula (I), the mark "*" indicates a position at which the structure is bound to another atom or atomic group, and at least one O atom in a phosphoric acid linkage may be substituted with an S atom;

a tautomer or stereoisomer of the compound; or a salt of the compound, the tautomer, or the stereoisomer.

The present invention also provides a labeling substance produced using the compound according to the present invention, a tautomer or stereoisomer of the compound, or a salt of the compound, the tautomer, or the stereoisomer.

The present invention also provides a detection method including the step of: detecting a substance to be detected by bringing the labeling substance according to the present invention into contact with the substance to be detected.

Effects of the Invention

The compound of the present invention is not a thymine derivative but a cytosine derivative. Thus, the compound of the present invention can be used as a reagent, other than thymine derivatives, for synthesizing nucleic acids (such as DNA and RNA, for example), so that it can alleviate the restrictions on the sequence design of modified nucleic acid (such as DNA and RNA, for example) oligomers. Furthermore, according to the present invention, it is also possible to provide a nucleic acid and labeling substance that can be produced using the compound of the present invention and a detection method using the labeling substance.

BRIEF DESCRIPTION OF DRAWINGS

FIG. 1 shows performances of modified DNA oligomers in an isothermal nucleic acid amplification method in an example of the present invention.

MODE FOR CARRYING OUT THE INVENTION

Hereinafter, the present invention will be described more specifically with reference to illustrative examples. It is to be noted, however, that the present invention is not limited by the following descriptions.

The present invention also can be described as in the following items [1] to [38], for example. It is to be noted, however, that the present invention is by no means limited thereto.

[1] A compound represented by the following chemical formula (I); a tautomer or stereoisomer of the compound; or a salt of the compound, the tautomer, or the stereoisomer:

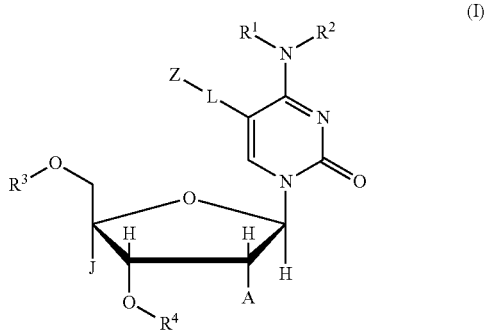

(I)

where in the chemical formula (I), $R^1$ and $R^2$ are each a Group 1 element or a protecting group of an amino group and may be identical to or different from each other, or alternatively, $R^1$ and $R^2$ together may form a protecting group of an amino group, $R^3$ is a Group 1 element or a protecting group of a hydroxy group, $R^4$ is a Group 1 element or —$PR^5R^6R^7R^8$ ($R^5$, $R^6$, $R^7$, and $R^8$ are each a Group 1 element, a lone electron pair, a Group 16 element, a Group 17 element, or a protecting group of a phosphorus atom, and may be identical to or different from each other), J is a hydrogen atom or an arbitrary atomic group, A is a hydrogen atom, a hydroxy group, an alkyl group, an aralkyl group, an alkoxy group, an electron-withdrawing group, a silylene group, or a sulfide group, or alternatively, J and A together may form a linker, L is a single bond or a linker (a linking atom or a linking atomic group), the main chain length (the number of main chain atoms) of the linker is arbitrary, L may or may not contain each of C, N, O, S, P, and Si in the main chain, and may or may not contain each of a single bond, a double bond, a triple bond, an amide bond, an ester bond, a disulfide bond, an imino group, an ether bond, a thioether bond, and a thioester bond in the main chain, and Z is an atomic group that can form a peptide bond with a labeling compound, or is an atom or atomic group including a label.

[2] The compound described in the item [1], wherein, in the chemical formula (I), Z is an atomic group that can form a peptide bond with a labeling compound, and the atomic group that can form a peptide bond with the labeling compound is an atomic group including an ester group or a carbonyl group or is a carboxylic halide group (halocarbonyl group);

a tautomer or stereoisomer of the compound; or a salt of the compound, the tautomer, or the stereoisomer.

[3] The compound described in the item [1], wherein, in the chemical formula (I), Z is an atomic group that can form a peptide bond with a labeling compound, and the atomic group that can form a peptide bond with the labeling compound is an N-hydroxy succinimidyl ester group represented by the following chemical formula (NHSE):

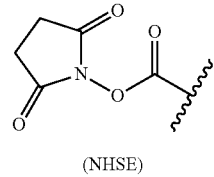 [SMILES: *C(=O)ON1C(=O)CCC1=O]

(NHSE)

where in the chemical formula (NHSE), a wavy line indicates a position at which the atomic group is bound to L;

a tautomer or stereoisomer of the compound; or a salt of the compound, the tautomer, or the stereoisomer.

[4] The compound described in any of the items [1] to [3], wherein, in the chemical formula (I), L is (—CH=CH—) or (—C≡C—);

a tautomer or stereoisomer of the compound; or a salt of the compound, the tautomer, or the stereoisomer.

[5] The compound described in any of the items [1] to [4], wherein, in the chemical formula (I), J is a hydrogen atom, an alkyl group, an alkoxy group, an amino group, a sulfil group, or a silyl group, and each main chain carbon atoms of the alkyl group and alkoxy group may be N, O, S, P, or Si, instead of the carbon atom, and A is a hydrogen atom, a hydroxy group, an alkyl group, an aralkyl group, an alkoxy group, an electron-withdrawing group, a silylene group, or a sulfide group, or alternatively, J and A together may form a linker, and J and A are each $CH_2$, NH, O, or S and may be identical to or different from each other;

a tautomer or stereoisomer of the compound; or a salt of the compound, the tautomer, or the stereoisomer.

[6] The compound described in any of the items [1] to [5], wherein, in A in the chemical formula (I), the alkyl group is a methyl group, an ethyl group, a propyl group, a butyl group, a pentyl group, or a hexyl group, the aralkyl group is a benzyl group, the alkoxy group is a methoxy group, and the electron-withdrawing group is a halogen, a trifluoromethyl group, or a fluoroalkyl group;

a tautomer or stereoisomer of the compound; or a salt of the compound, the tautomer, or the stereoisomer.

[7] The compound described in any of the items [1] to [6], wherein the structure represented by the chemical formula (I) is a structure represented by the following chemical formula 1a:

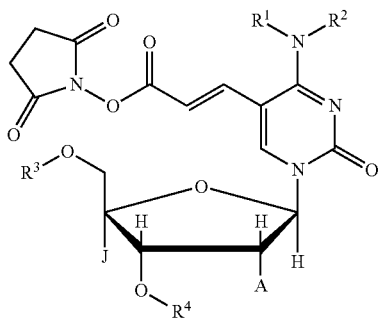

1a where in the chemical formula 1a, $R^1$, $R^2$, $R^3$, $R^4$, J, and A are identical to those in the chemical formula (I);

a tautomer or stereoisomer of the compound; or a salt of the compound, the tautomer, or the stereoisomer.

[8] The compound described in any of the items [1] to [6], wherein the structure represented by the chemical formula (I) is a structure represented by the following chemical formula 1:

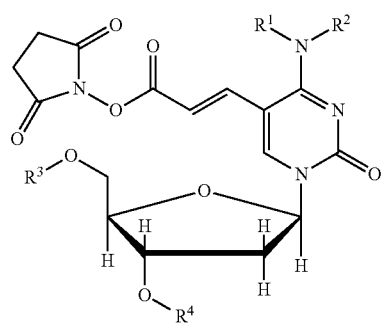

1 where in the chemical formula 1, $R^1$, $R^2$, $R^3$, and $R^4$ are identical to those in the chemical formula (I);

a tautomer or stereoisomer of the compound; or a salt of the compound, the tautomer, or the stereoisomer.

[9] The compound described in any of the items [1] to [8], wherein the structure represented by the chemical formula (I) is a structure represented by the following chemical formula (Ia) or (Ib);

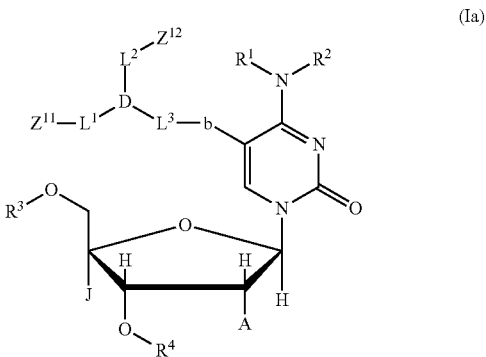

(Ia)

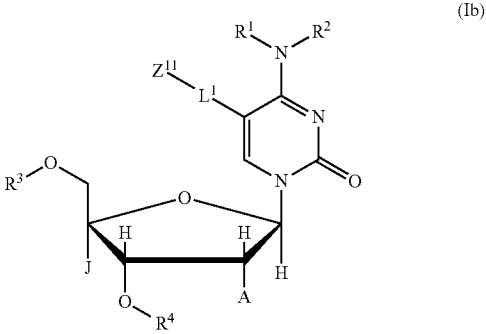

(Ib)

where in the chemical formulae (Ia) and (Ib), $R^1$, $R^2$, $R^3$, $R^4$, J, and A are identical to those in the chemical formula (I), in the chemical formula (Ia), $Z^{11}$ and $Z^{12}$ are each a fluorescent dye moiety, and may be identical to or different from each other, $L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR, and R is a hydrogen atom, an alkyl group, or an arbitrary substituent, b is a single bond, a double bond, or a triple bond, or alternatively, $L^3$ and b may not be present and D may be bonded directly to a cytosine ring, and in the chemical formula (Ib), $Z^{11}$ and $L^1$ are identical to those in the chemical formula (Ia);

a tautomer or stereoisomer of the compound; or a salt of the compound, the tautomer, or the stereoisomer.

[10] The compound described in the item [9], wherein, in the chemical formulae (Ia) and (Ib), the main chain length (the number of main chain atoms) of each of $L^1$, $L^2$, and $L^3$ is an integer of 2 or more;

a tautomer or stereoisomer of the compound; or a salt of the compound, the tautomer, or the stereoisomer.

[11] The compound described in the item [9] or [10], wherein, in the chemical formulae (Ia) and (Ib), $Z^{11}$ and $Z^{12}$ are each a fluorescent dye moiety that exhibits an exciton effect;
a tautomer or stereoisomer of the compound; or
a salt of the compound, the tautomer, or the stereoisomer.

[12] The compound described in any of the items [9] to [11], wherein, in the formulae (Ia) and (Ib), $Z^{11}$ and $Z^{12}$ are each independently a group derived from any one of thiazole orange, oxazole yellow, cyanine, hemicyanine, Cy5, other cyanine dyes, methyl red, azo dyes, biotin, and derivatives thereof;
a tautomer or stereoisomer of the compound; or
a salt of the compound, the tautomer, or the stereoisomer.

[13] The compound described in any of the items [9] to [12], wherein, in the formulae (Ia) and (Ib),
$Z^{11}$ and $Z^{12}$ are each independently an atomic group represented by any one of the following formulae (7) to (9):

(7)

(8)

(9)

where in the formulae (7) to (9),
$X^1$ and $X^2$ are S, O, or Se,
n" is 0 or a positive integer,
$R^1$ to $R^{10}$ and $R^{13}$ to $R^{21}$ are each independently a hydrogen atom, a halogen atom, a lower alkyl group, a lower alkoxyl group, a nitro group, or an amino group,
one of $R^{11}$ and $R^{12}$ is a linking group that is bound to $L^1$ or $L^2$ in the formulae (Ia) and (Ib), and the other is a hydrogen atom or a lower alkyl group,
when a plurality of $R^{15}$s are present in the formula (7), (8), or (9), they may be identical to or different from each other,
when a plurality of $R^{16}$s are present in the formula (7), (8), or (9), they may be identical to or different from each other, and
$X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively;
a tautomer or stereoisomer of the compound; or
a salt of the compound, the tautomer, or the stereoisomer.

[14] The compound described in the item [13], wherein, in $R^1$ to $R^{21}$ in the formulae (7) to (9), the lower alkyl group is a linear or branched alkyl group with a carbon number of 1 to 6, and the lower alkoxyl group is a linear or branched alkoxyl group with a carbon number of 1 to 6;
a tautomer or stereoisomer of the compound; or
a salt of the compound, the tautomer, or the stereoisomer.

[15] The compound described in the item [13] or [14], wherein, in $R^{11}$ and $R^{12}$ in the formulae (7) to (9), the linking group is a polymethylene carbonyl group with a carbon number of 2 or more and is bound to $L^1$ or $L^2$ in the formulae (Ia) and (Ib) in a carbonyl group moiety;
a tautomer or stereoisomer of the compound; or
a salt of the compound, the tautomer, or the stereoisomer.

[16] The compound described in any of the items [13] to [15], wherein, in the formulae (Ia) and (Ib),
$Z^{11}$ and $Z^{12}$ are each independently an atomic group represented by the formula (7) or (8), and
$Z^{11}$ and $Z^{12}$ represented by the formula (7) or (8) is a group represented by the following formula (19) or (20):

(19)

(20)

where in the formulae (19) and (20),
$X^1$, $R^1$ to $R^{10}$, $R^{13}$ and $R^{14}$, and $R^{11}$ and $R^{12}$ are identical to those in the formulae (7) to (9);
a tautomer or stereoisomer of the compound; or
a salt of the compound, the tautomer, or the stereoisomer.

[17] The compound described in the item [16], wherein
$Z^{11}$ and $Z^{12}$ are each independently an atomic group represented by the above formula (19),
where in the formula (19),
$X^1$ is S,
$R^1$ to $R^{10}$ are hydrogen atoms, and
one of $R^{11}$ and $R^{12}$ is a linking group that is bound to $L^1$ or $L^2$ in the formulae (Ia) and (Ib), and the other is a methyl group;
a tautomer or stereoisomer of the compound; or
a salt of the compound, the tautomer, or the stereoisomer.

[18] The compound described in the item [16], wherein, in the formulae (Ia) and (Ib),
$Z^{11}$ and $Z^{12}$ are each independently an atomic group represented by the above formula (19),
where in the formula (19),
$X^1$ is S,
$R^1$, $R^4$, $R^5$, $R^6$, $R^7$, $R^9$, and $R^{10}$ are hydrogen atoms,
$R^2$, $R^3$, and $R^{12}$ are methyl groups,
$R^8$ is a halogen atom, and
$R^{11}$ is a linking group that is bound to $L^1$ or $L^2$ in the formulae (Ia) and (Ib);
a tautomer or stereoisomer of the compound; or
a salt of the compound, the tautomer, or the stereoisomer.

[19] The compound described in the item [13], wherein, in the formulae (Ia) and (Ib),
$Z^{11}$ and $Z^{12}$ are each independently an atomic group represented by the above formula (7),
where in the formula (7),
$X^1$ is S,
n is 1,
$R^1$ to $R^{10}$, $R^{15}$, $R^{16}$, and $R^{17}$ are hydrogen atoms,
$R^{11}$ is a linking group that is bound to $L^1$ or $L^2$ in the formulae (Ia) and (Ib), and
$R^{12}$ is a methyl group;
a tautomer or stereoisomer of the compound; or
a salt of the compound, the tautomer, or the stereoisomer.

[20] The compound described in any of the items [9] to [12], wherein, in the formulae (Ia) and (Ib),
$Z^{11}$ and $Z^{12}$ are each independently an atomic group represented by any one of the following formulae:

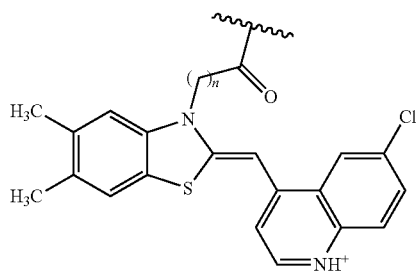

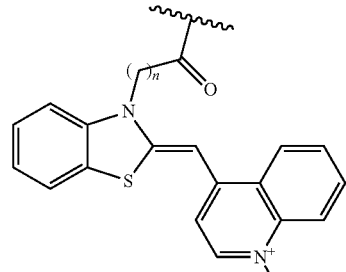

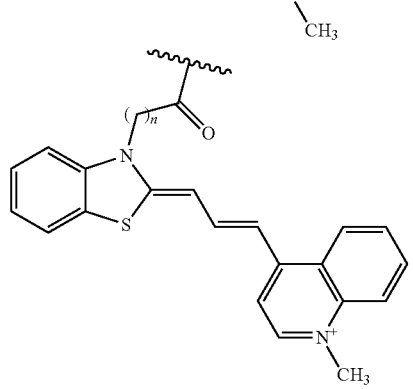

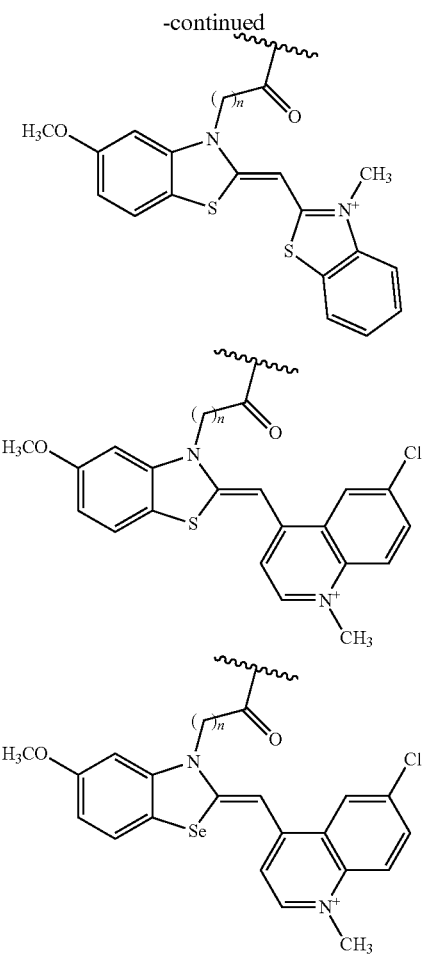

where in each of the above chemical formulae, a wavy line indicates a position at which the atomic group is bound to $L^1$ or $L^2$, and
n is a positive integer;
a tautomer or stereoisomer of the compound; or
a salt of the compound, the tautomer, or the stereoisomer.

[21] The compound described in the item [20], wherein the linker length n is in the range from 2 to 6;
a tautomer or stereoisomer of the compound; or
a salt of the compound, the tautomer, or the stereoisomer.

[22] The compound described in the item [9] or [10], wherein, in the formulae (Ia) and (Ib), $Z^{11}$ and $Z^{12}$ are each independently an atomic group represented by any one of the following formulae:

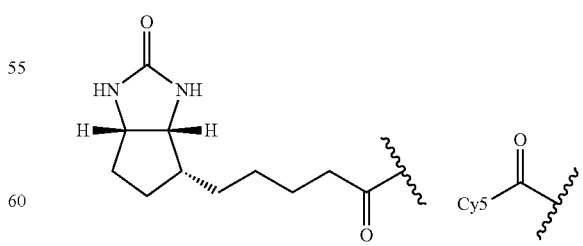

where in each of the above chemical formulae, a wavy line indicates a position at which the atomic group is bound to $L^1$ or $L^2$, and Cy5 is a group derived from a cyanine dye Cy5;
a tautomer or stereoisomer of the compound; or
a salt of the compound, the tautomer, or the stereoisomer.

[23] The compound described in any of the items [9] to [22], wherein the structure represented by the formula (Ia) is a structure represented by the following formula (Ia-1), and the structure represented by the formula (Ib) is a structure represented by the following formula (Ib-1);

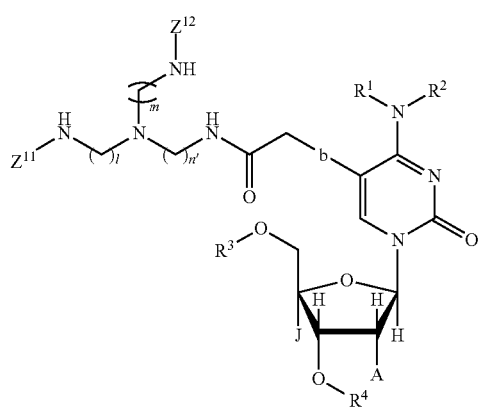
(Ia-1)

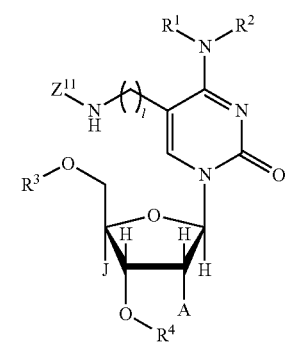
(Ib-1)

where in the formulae (Ia-1) and (Ib-1), l, m, and n' are arbitrary, l, m, and n' may be identical to or different from each other, l, m, and n' each may or may not contain each of C, N, O, S, P, and Si in a main chain thereof, and l, m, and n' each may or may not contain each of a single bond, a double bond, a triple bond, an amide bond, an ester bond, a disulfide bond, an imino group, an ether bond, a thioether bond, and a thioester bond in the main chain, and $R^1$, $R^2$, $R^3$, $R^4$, J, A, $Z^{11}$, $Z^{12}$, and b are identical to those in the formulae (Ia) and (Ib);

a tautomer or stereoisomer of the compound; or a salt of the compound, the tautomer, or the stereoisomer.

[24] The compound described in the item [23], wherein, in the formulae (Ia-1) and (Ib-1), l, m, and n' are each an integer of 2 or more;

a tautomer or stereoisomer of the compound; or a salt of the compound, the tautomer, or the stereoisomer.

[25] A nucleic acid including at least one structure represented by the following chemical formula (I-2):

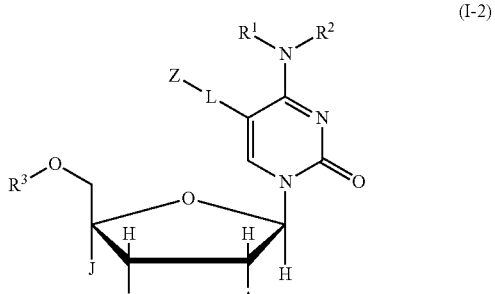
(I-2)

where in the chemical formula (I-2), $R^1$, $R^2$, $R^3$, J, A, L, and Z are identical to those in the chemical formula (I) in any one of claims 1 to 23, and the mark "*" indicates a position at which the structure is bound to another atom or atomic group;

a tautomer or stereoisomer of the compound; or a salt of the compound, the tautomer, or the stereoisomer.

[26] The nucleic acid described in the item [25], represented by the following chemical formula 1001:

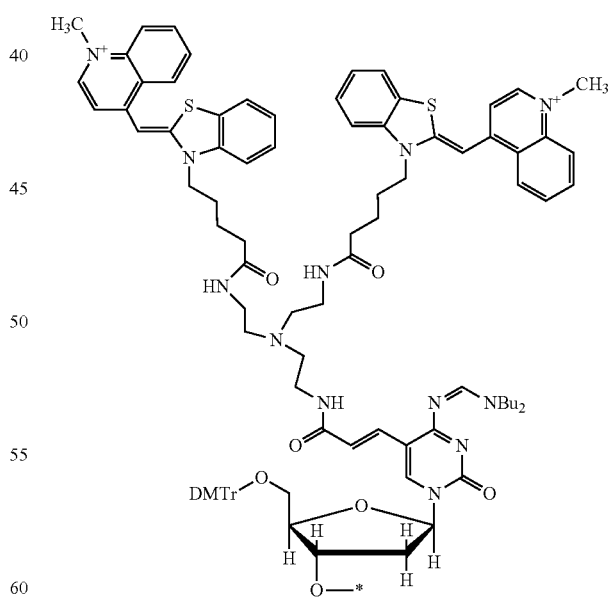
1001 where in the chemical formula 1001, the mark "*" is identical to that in the chemical formula (I-2);

a tautomer or stereoisomer of the compound; or a salt of the compound, the tautomer, or the stereoisomer.

[27] A nucleic acid including at least one structure represented by the following chemical formula (II):

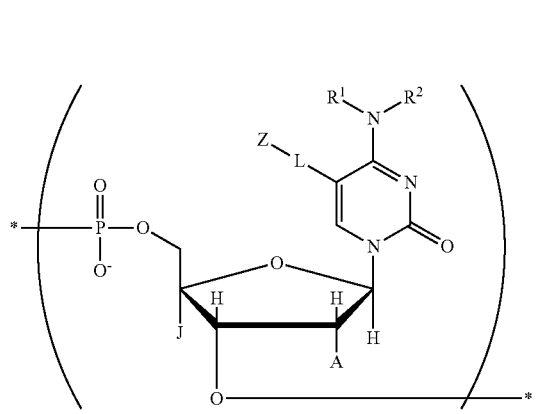

(II)

where in the chemical formula (II), $R^1$, $R^2$, J, A, L, and Z are identical to those in the chemical formula (I) in any one of claims 1 to 23, the mark "*" indicates a position at which the structure is bound to another atom or atomic group, and at least one O atom in a phosphoric acid linkage may be substituted with an S atom;

a tautomer or stereoisomer of the compound; or a salt of the compound, the tautomer, or the stereoisomer.

[28] The nucleic acid described in the item [27], wherein the structure represented by the chemical formula (II) is a structure represented by the following chemical formula 1b:

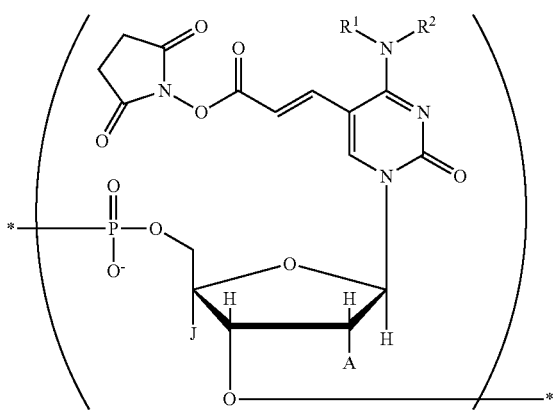

1b where in the chemical formula 1b, $R^1$, $R^2$, J, and A are identical to those in the chemical formula (II), and at least one O atom in a phosphoric acid linkage may be substituted with an S atom;

a tautomer or stereoisomer of the compound; or a salt of the compound, the tautomer, or the stereoisomer.

[29] The nucleic acid described in the item [27], wherein the structure represented by the chemical formula (II) is a structure represented by the following chemical formula 1c;

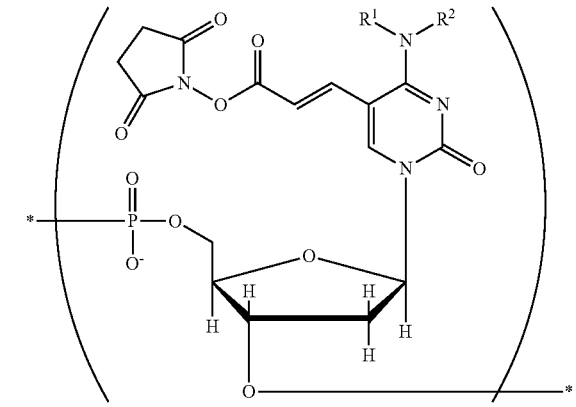

1c where in the chemical formula 1c, $R^1$ and $R^2$ are identical to those in the chemical formula (II), and at least one O atom in a phosphoric acid linkage may be substituted with an S atom;

a tautomer or stereoisomer of the compound; or a salt of the compound, the tautomer, or the stereoisomer.

[30] The nucleic acid described in the item [27], wherein the structure represented by the chemical formula (II) is a structure represented by the following chemical formula (IIa) or (IIb);

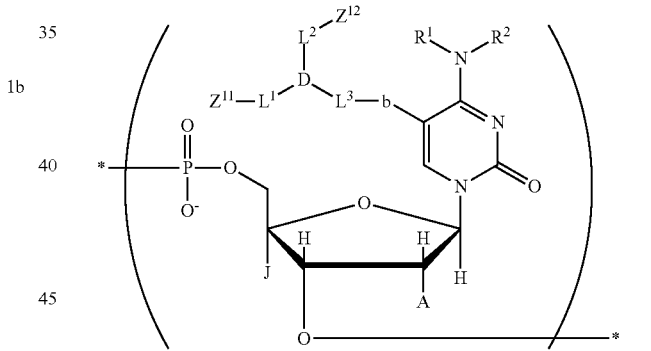

(IIa)

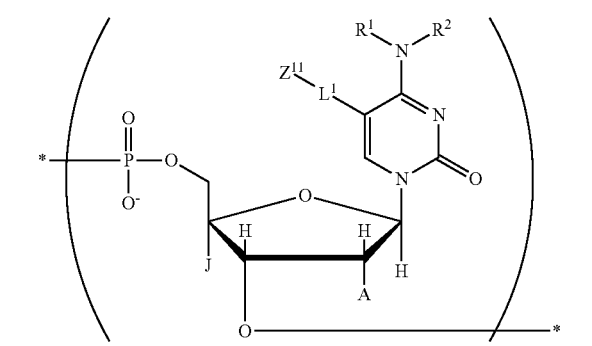

(IIb)

where in the chemical formulae (IIa) and (IIb), $R^1$, $R^2$, J, and A are identical to those in the chemical formula (II), in the chemical formula (IIa), $Z^{11}$ and $Z^{12}$ are each a fluorescent dye moiety, and may be identical to or different from each other, $L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR, and R is a hydrogen atom, an alkyl group, or an arbitrary substituent, b is a single bond, a double bond, or a triple bond, or alternatively, $L^3$ and b may not be present and D may be bonded directly to a cytosine ring, in the chemical formula (IIb), $Z^{11}$ and $L^1$ are identical to those in the chemical formula (IIa), and in the chemical formulae (IIa) and (IIb), at least one O atom in a phosphoric acid linkage may be substituted with an S atom;

a tautomer or stereoisomer of the compound; or a salt of the compound, the tautomer, or the stereoisomer.

[31] The nucleic acid described in the item [30], wherein
the structure represented by the formula (IIa) is a structure represented by the following formula (IIa-1), and
the structure represented by the formula (IIb) is a structure represented by the following formula (IIb-1);

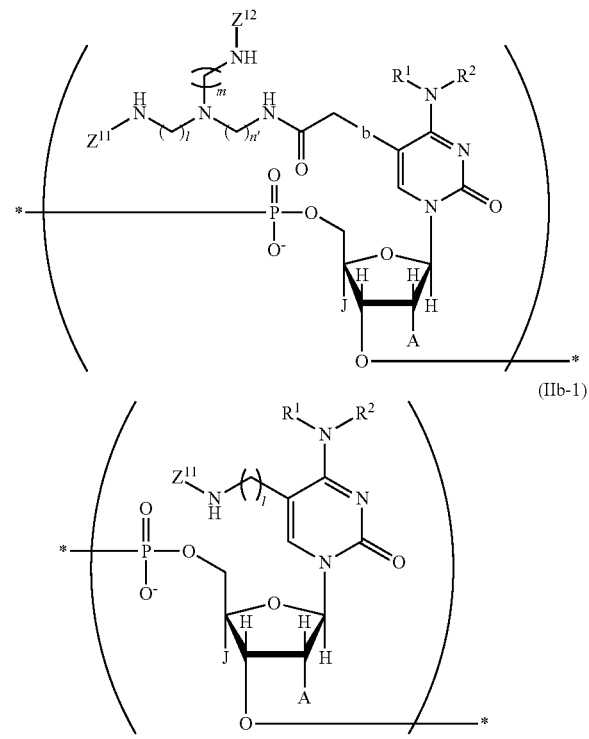

where in the formulae (IIa-1) and (IIb-1), l, m, and n' are arbitrary, l, m, and n' may be identical to or different from each other, l, m, and n' each may or may not contain each of C, N, O, S, P, and Si in a main chain thereof, and l, m, and n' each may or may not contain each of a single bond, a double bond, a triple bond, an amide bond, an ester bond, a disulfide bond, an imino group, an ether bond, a thioether bond, and a thioester bond in the main chain, $R^1$, $R^2$, J, A, $Z^{11}$, $Z^{12}$, and b are identical to those in formulae (IIa) and (IIb), and in the formulae (IIa-1) and (IIb-1), at least one O atom in a phosphoric acid linkage may be substituted with an S atom;

a tautomer or stereoisomer of the compound; or a salt of the compound, the tautomer, or the stereoisomer.

[32] The nucleic acid described in the item [31], wherein, in the formulae (IIa-1) and (IIb-1), l, m, and n' are each an integer of 2 or more;

a tautomer or stereoisomer of the compound; or a salt of the compound, the tautomer, or the stereoisomer.

[33] The nucleic acid described in any of the items [27] to [32], including at least one nucleotide structure represented by the following chemical formula 1000:

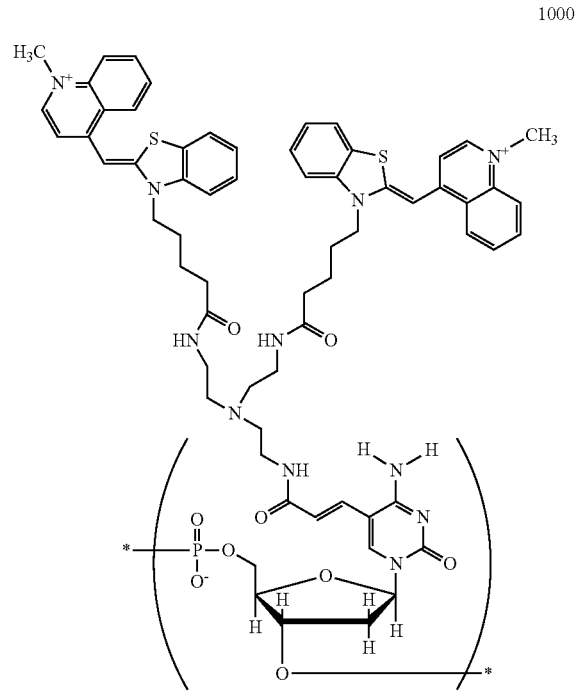

a tautomer or stereoisomer of the compound; or a salt of the compound, the tautomer, or the stereoisomer.

[34] A labeling substance produced using the compound described in any of the items [1] to [24], a tautomer or stereoisomer of the compound, or a salt of the compound, the tautomer, or the stereoisomer.

[35] The labeling substance described in the item [34], wherein
the labeling substance is a labeling mononucleotide, a labeling oligonucleotide, a labeling nucleic acid, or a labeling nucleic acid derivative.

[36] The labeling substance described in the item [34] or [35], including:
the nucleic acid described in the item [27], wherein Z in the chemical formula (II) is labeled, or
the nucleic acid described in any of the items [30] to [33].

[37] A detection method including the step of
detecting a substance to be detected by bringing the labeling substance described in any of the items [34] to [36] into contact with the substance to be detected.

[38] The detection method described in the item [37], wherein
the labeling substance includes a fluorescent dye moiety,
when the fluorescent dye moiety comes in contact with the substance to be detected, the fluorescent dye moiety emits light or light emitted from the fluorescent dye is quenched, and
the substance to be detected is detected based on the presence or absence of the light emitted from the fluorescent dye moiety.

[Compound of the Present Invention]

The inventors of the present invention conducted diligent studies focusing on the improvement of modified DNA oligomers. As a result, they developed a reagent for synthesizing DNA, which is a base other than commercially available thymine derivatives. With the use of this reagent, the binding of a functional molecule such as a dye can be achieved in a DNA synthesizer, which allows the purification step to be shortened drastically. It is to be noted, however, that the compound according to the present invention is not limited to compounds for synthesizing DNA, but also includes, for example, compounds for synthesizing other nucleic acids such as RNA.

In order to solve the above-described problems, the inventors of the present invention designed and synthesized a nucleic acid base that has the same reactive site as commercially available thymine derivatives. That is, the compound according to the present invention (the nucleic acid base derivative according to the present invention) is a compound characterized in that, as represented by the above chemical formula (I), it includes an NHS group as an active site, a tautomer or stereoisomer thereof, or a salt thereof.

In the chemical formula (I), the main chain length (the number of main chain atoms) of L preferably is an integer of 2 or more. The upper limit thereof is not particularly limited, and is, for example, 100 or less, more preferably 30 or less, and particularly preferably 10 or less. The structure of the linker L and the structure of the atomic group Z containing a label are not particularly limited, and they may be the same as those in the nucleic acid of the present invention (the chemical formula (II)) to be described below, for example.

In the compound of the present invention (the chemical formula (I)), the protecting group is not particularly limited, and a protecting group suitable for each functional group can be used (see the reference document: Protective groups in organic chemistry, Wiley-inter science, for example). In the present invention, the protecting group of an amino group is not particularly limited. Examples thereof include a trifluoroacetyl group, a formyl group, a C1-6 alkyl-carbonyl group (for example, acetyl and ethylcarbonyl), a C1-6 alkyl sulfonyl group, a tert-butyloxycarbonyl group (hereinafter also referred to as "Boc"), a benzyloxycarbonyl group, an allyloxycarbonyl group, a fluorenylmethyloxy carbonyl group, an arylcarbonyl group (for example, phenylcarbonyl and naphthylcarbonyl), an arylsulfonyl group (for example, phenylsulfonyl and naphthylsulfonyl), a C1-6 alkyloxycarbonyl group (for example, methoxycarbonyl and ethoxycarbonyl), a C7-10 aralkylcarbonyl group (for example, benzylcarbonyl), a methyl group, and an aralkyl group (for example, benzyl, diphenylmethyl, and trityl groups). These groups may be substituted with, for example, one to three halogen atoms (for example, fluorine, chlorine, or bromine) or nitro groups. Specific examples thereof include a p-nitrobenzyloxycarbonyl group, a p-chlorobenzyloxycarbonyl group, an m-chlorobenzyloxycarbonyl group, and a p-methoxybenzyloxycarbonyl group. In the present invention, the protecting group of a hydroxyl group (including one capable of being deprotected with acid) is not particularly limited. Examples thereof include a dimethoxytrityl group, a monomethoxytrityl group, and a pixyl group.

In the chemical formula (I), $R^1$ and $R^2$ may be different atoms (atomic groups) or the same atoms (atomic groups). When $R^1$ and $R^2$ are different atoms (atomic groups), they each may be independently a hydrogen atom, a lithium atom, a sodium atom, a potassium atom, a rubidium atom, a cesium atom, an alkyl group, an aralkyl group, an aryl group, or an acyl group. When $R^1$ and $R^2$ are the same atoms (atomic groups), they may be the same cyclic alkyl groups or the same amidine protecting groups, for example. Alternatively, $R^1$ and $R^2$ together may form a protecting group of an amino group. In this case, examples of the protecting group of an amino group include substituents represented by $=C-NR^{100}_2$. $R^{100}$ are each a linear or branched alkyl group with an oxygen number of 1 to 20, and they may be identical to or different from each other. Specific examples of $R^{100}$ include an n-butyl group. $R^3$ may be, for example, a hydrogen atom, a lithium atom, a sodium atom, a potassium atom, a rubidium atom, a cesium atom, an alkyl group, an aralkyl group, an aryl group, an acyl group, a silyl group, or the like. $R^4$ may be, for example, a hydrogen atom, a lithium atom, a sodium atom, a potassium atom, a rubidium atom, a cesium atom, an alkyl group, an aralkyl group, an aryl group, an acyl group, a silyl group, or the like. $R^5$, $R^6$, $R^7$, and $R^8$ may be lone electron pairs, different atoms (atomic groups), or the same atoms (atomic groups). When $R^5$, $R^6$, $R^7$, and $R^8$ are different atomic groups, they each may be independently a hydrogen atom, a lithium atom, a sodium atom, a potassium atom, a rubidium atom, a cesium atom, a fluorine atom, a chlorine atom, a bromine atom, an iodine atom, an alkyl group, an alkoxy the same atoms (atomic groups), they may be, for examples, oxygen atoms, sulfur atoms, selenium atoms, tellurium atoms, the same cyclic alkyl groups, the same amidine protecting groups, the same cyclic ether groups, or the same cyclic amino groups.

In the present invention, the "alkyl group" is not particularly limited, and may be, for example, an alkyl group with a carbon number of 1 to 20. Specific examples thereof include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. The same applies to groups containing an alkyl group in their structures (alkoxy groups, aralkyl groups, etc.). The "aryl group" is not particularly limited, and may be, for example, an aryl group with a carbon number of 5 to 24. Specific examples thereof include a phenyl group, a naphthyl group, a tolyl group, and an anisyl group. The same applies to groups containing an aryl group in their structures (aralkyl groups etc.). In the present invention, the "aralkyl group" is not particularly limited, and may be, for example, a benzyl group, a diphenylmethyl group, a trityl group, a phenethyl group, or the like. The "acyl group" is not particularly limited, and may be, for example, a formyl group, an acetyl group, a propionyl group, an isobutyryl group, a valeryl group, an isovaleryl group, a pivaloyl group, a hexanoyl group, a cyclohexanoyl group, a benzoyl group, an ethoxycarbonyl group, or the like. The "amidine protecting group" is not particularly limited, and may be, for example, a dimethylformamidine group, a diethylformamidine group, a dipropylformamidine group, dibutylformamidine group, or the like. The "cyclic alkyl group" is not particularly limited, and may be a cyclic butyl group, a cyclic pentyl group, or the like. The "silyl group" is not particularly limited, and may be a trimethylsilyl group, a triethylsilyl group, triisopropylsilyl group, a tert-butyldimethylsilyl group, a tert-butyldiphenylsilyl group, or the like. The "cyclic ether group" is not particularly limited, and may be a 1,2-dioxyethyl group, 1,3-dioxypropyl group, or the like. The "cyclic amino group" is not particularly limited, and may be a 1,2-diaminoethyl group, a 1,3-diaminopropyl group, or the like. The "Group 17 element" refers to any halogen element, and examples thereof include fluorine, chlorine, bromine, and iodine. The "Group 16 element" refers to any chalcogen element, and examples thereof include sulfur, selenium, and tellurium.

When the compound of the present invention and the nucleic acid and labeling substance of the present invention have an isomer such as a tautomer or a stereoisomer (e.g., a geometric isomer, a conformer, or an optical isomer), any of the isomers can be used for the present invention. The salt of the compound or nucleic acid may be an acid addition salt, and also may be a base addition salt. Furthermore, the acid that forms the acid addition salt may be an inorganic acid or an organic acid, and the base that forms the base addition salt may be an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzene-sulfonic acid, carbonic acid, succinic acid, citric acid, benzoic acid, and acetic acid. The inorganic base is not particularly limited, and examples thereof include ammonium hydroxide, alkali metal hydroxide, alkaline earth metal hydroxide, carbonate, and hydrogen carbonate. More specific examples thereof include sodium hydroxide, potassium hydroxide, potassium carbonate, sodium carbonate, sodium bicarbonate, potassium hydrogencarbonate, calcium hydroxide, and calcium carbonate. The organic base also is not particularly limited, and examples thereof include ethanolamine, triethylamine, and tris(hydroxymethyl)aminomethane. The method for producing salts thereof also is not particularly limited. They can be produced by, for example, adding the acid or base as described above as appropriate by a known method. Furthermore, when the substituent or the like has an isomer, any of the isomers can be used. For instance, in the case of a "naphthyl group", it may be a 1-naphthyl group or a 2-naphthyl group.

The compound of the present invention may be, for example, a NHS-carboxylated cytosine derivative represented by the chemical formula 1. This NHS-carboxylated cytosine derivative has the same reactive site as commercially available NHS-carboxylated thymine derivatives. Thus, the reactivity and the stability of the compound of the present invention are equivalent to those of the commercially available NHS-carboxylated thymine derivatives, and the compound of the present invention can be stored in the air at room temperature. Heretofore, if DNA oligomers to be modified do not have thymine in their sequences, the synthesis of such modified DNA oligomers was not possible. The development of this NHS-carboxylated cytosine derivative enables the synthesis of such DNA oligomers, for example.

The method for producing the compound of the present invention is not particularly limited. For example, the compound of the present invention may be produced using any of known synthesis methods (production methods) as appropriate or with reference to such known synthesis methods. Specifically, the compound of the present invention may be produced, for example, by any of synthesis methods described in the following examples, methods equivalent to these synthesis methods, or with reference to these synthesis methods.

For example, the compound without a label introduced thereto (the compound represented by the chemical formula (I) where Z is an atomic group that can form a peptide bond with a labeling compound and does not contain a label) can be produced by a method equivalent to the synthesis method of Compound 4 in the following Example 1 or with reference to the synthesis method.

Next, as a labeling compound for introducing a label, for example, a labeling compound represented by the following chemical formula 5 can be obtained by reacting Compound 109 shown in the following Scheme 1 with a compound obtained by introducing a protecting group to one amino group in tris(2-aminoethyl)amine.

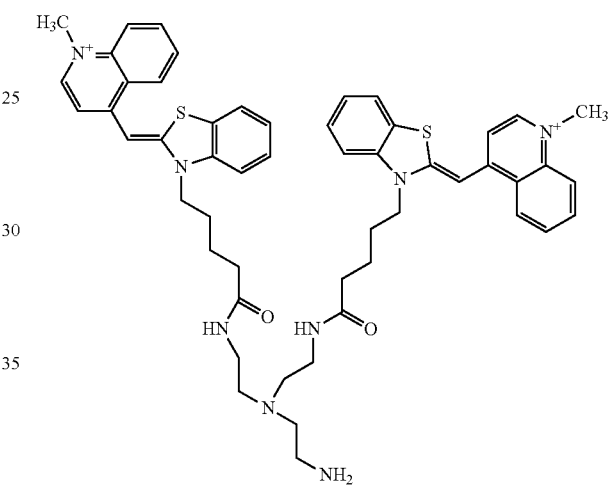

5

Scheme 1

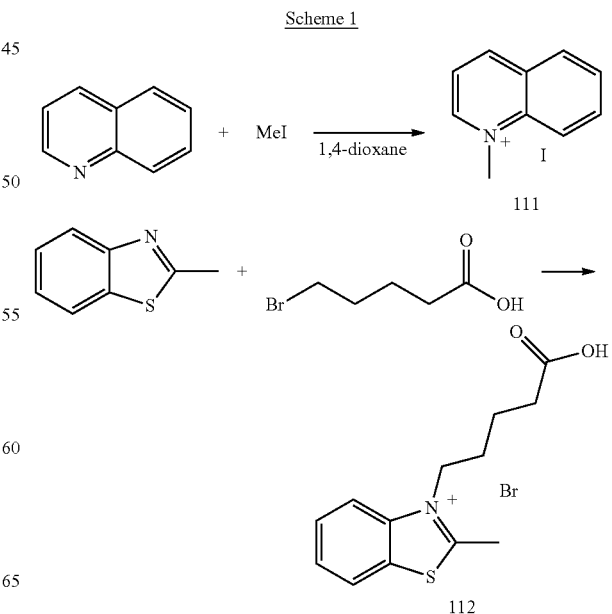

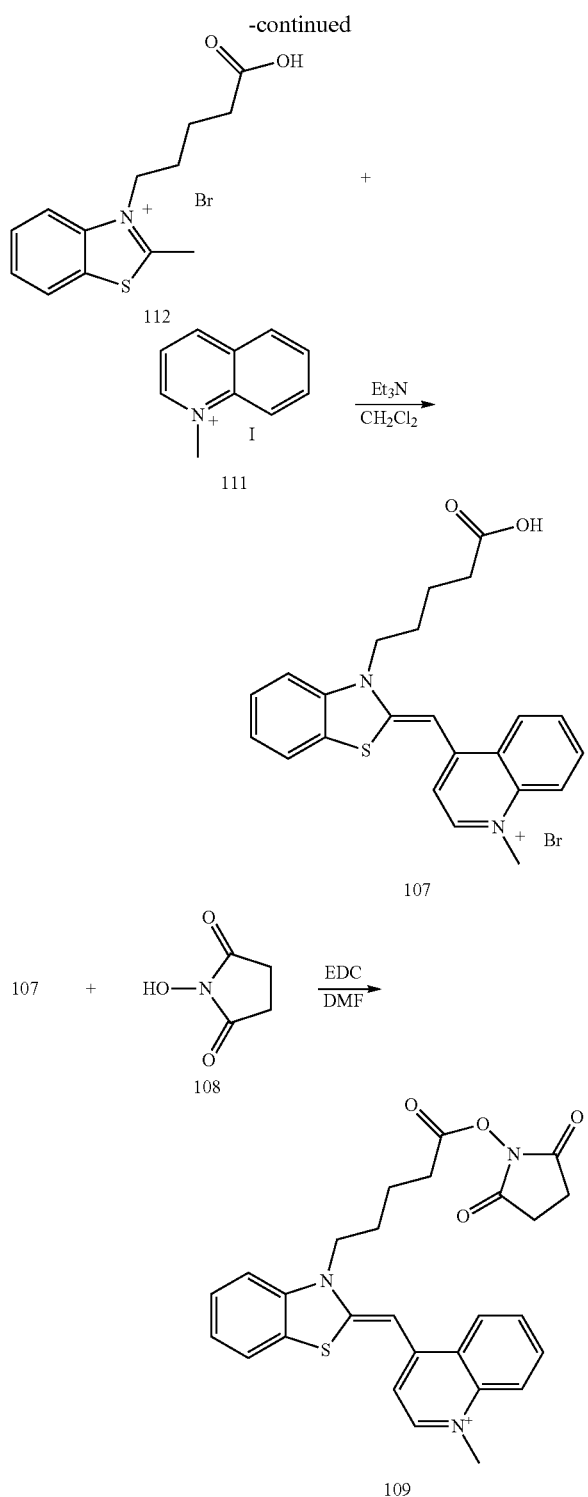

of methyl iodide were added to 42 ml of anhydrous dioxane, and the resultant mixture was stirred at 150° C. for 1 hour. Thereafter, it was filtered and a precipitate was collected. Then, the precipitate was washed with ether and petroleum ether, and then dried.

Thus, N-methylquinolinium iodide (Compound 111) was obtained.

(2) Synthesis of 3-(4-carboxybutyl)-2-methylbenzothiazolium bromide (Compound 112)

8 ml of 2-methylbenzothiazole (FW 149.21, d=1.173) and 9.4 g of 5-bromovaleric acid (5-bromopentanoic acid) (FW 181.03) were stirred at 110° C. for 16 hours. The crude product was cooled to room temperature and a solid thus produced was suspended in 20 ml of methanol, and 40 ml of ether further was added thereto. The precipitate thus produced was filtered and then washed with dioxane until the odor of 2-methylbenzothiazole was removed. This further was washed with ether and then dried under reduced pressure. Thus 9.8 g of white powder was obtained. Thereafter, $^1$HNMR of this white powder was measured. As a result, it was found to be a mixture of 3-(4-carboxybutyl)-2-methylbenzothiazolium bromide (Compound 112), which was the desired substance whose 2-position had been alkylated, and 3-(4-carboxybutyl)-benzothiazolium bromide whose 2-position had not been alkylated. The peak ratio of proton was non-alkylated:alkylated=10:3. This crude product was used for the next reaction without further being treated.

(3) Synthesis of 1-methyl-4-[{3-(4-carboxybutyl)-2(3H)-benzothiazolylidene}methyl]quinolinium bromide (Compound 107)

2.18 g of the crude product containing 3-(4-carboxybutyl)-2-methylbenzothiazolium bromide (Compound 112) obtained in (2) above and 700 mg of N-methylquinolinium iodide (Compound 111) (FW 271.10) were stirred in 10 ml of methylene chloride at 25° C. for 2 hours in the presence of 3.6 ml of triethylamine (FW 101.19, d=0.726). Thereafter, 50 ml of ether was added thereto and a precipitate produced thereby was filtered, washed with ether, and then dried under reduced pressure. The precipitate was suspended in 50 ml of ultrapure water, which was filtered, washed with ultrapure water, and then dried under reduced pressure. Further, the precipitate was suspended in 50 ml of acetonitrile, which was filtered, washed with acetonitrile, and then dried under reduced pressure. Thus, 307.5 mg of red powder was obtained (yield: 25.3%). This red powder was confirmed to be the desired substance (Compound 107) through a comparison in $^1$HNMR spectrum with the reference value.

Moreover, it was also possible to synthesize 3-(4-carboxybutyl)-2-methylbenzothiazolium bromide (Compound 112) and 1-methyl-4-[{3-(4-carboxybutyl)-2(3H)-benzothiazolylidene}methyl]quinolinium bromide (Compound 107) in the following manner. More specifically, first, 11.7 ml (92 mmol) of 2-methylbenzothiazole (FW 149.21, d=1.173) and 13.7 g (76 mmol) of 5-bromovaleric acid (5-bromopentanoic acid) (FW 181.03) were stirred at 150° C. for 1 hour. The crude product was cooled to room temperature and the solid thus produced was suspended in 50 ml of methanol. Further, 200 ml of ether was added thereto. The precipitate thus produced was filtered, washed with ether, and then dried under reduced pressure. Thus, 19.2 g of light purple powder was obtained. This powder was a mixture of the desired compound 112 (3-(4-carboxybutyl)-2-methylbenzothiazolium bromide) and 2-methylbenzothiazolium bromide. This mixture was subjected to $^1$HNMR (in DMSO-d6) measurement, and the yield of the desired compound 112 was calculated to be 9.82 g (14 mmol, 32%) from the peak area ratio between the peak at 8.5

An example of the synthesis method of Compound 109 according to Scheme 1 is shown below. Scheme 1 and the synthesis method according to Scheme 1 (to be described below) are described in Japanese Patent No. 4370385.

(1) Synthesis of N-methylquinolinium iodide (Compound 111)

First, N-methylquinolinium iodide (Compound 111) was synthesized according to the description in the above-described reference. Specifically, 2.4 ml of quinoline and 4 ml ppm (derived from the desired compound 112) and the peak at 8.0 ppm (derived from the 2-methylbenzothiazolium bromide). This mixture (crude product) was used for the next reaction without being purified. In the same manner as described above except that the 5-bromovaleric acid (5-bromopentanoic acid) was replaced with 4-bromobutyric acid (4-bromobutanoic acid), 3-(4-carboxypropyl)-2-methylbenzothiazolium bromide with a linker (a polymethylene chain linked to a carboxyl group) having a carbon number n of 3 was synthesized, which was obtained with a yield of 4%. Furthermore, in the same manner as described above except that 5-bromovaleric acid (5-bromopentanoic acid) was replaced with 6-bromohexanoic acid, 3-(4-carboxypentyl)-2-methylbenzothiazolium bromide with a linker (a polymethylene chain linked to a carboxyl group) having a carbon number n of 5 was synthesized, which was obtained with a yield of 35%. Still further, in the same manner as described above except that 5-bromovaleric acid (5-bromopentanoic acid) was replaced with 7-bromoheptanoic acid, 3-(4-carboxypropyl)-2-methylbenzothiazolium bromide with a linker (a polymethylene chain linked to a carboxyl group) having a carbon number n of 6 was synthesized, which was obtained with a yield of 22%.

Next, 1.36 g (5.0 mmol) of N-methylquinolinium iodide (Compound 111) (FW 271.10), 7.0 ml (50 mmol) of triethylamine (FW 101.19, d=0.726), and 100 ml of methylene chloride were added to 3.24 g of the mixture (crude product) containing Compound 112 (3-(4-carboxybutyl)-2-methylbenzothiazolium bromide) and 2-methylbenzothiazolium bromide. As a result, a transparent solution was obtained. This solution was stirred at 25° C. for 16 hours. Thereafter, the solvent was evaporated under reduced pressure. Acetone (200 ml) then was added to the residue and the precipitate obtained thereby was filtered, which then was washed with acetone. The residue thus obtained was dried under reduced pressure, and the red residue obtained after drying was washed with distilled water (50 ml). This further was filtered, which was washed with distilled water and then dried under reduced pressure. Thus, the desired substance (Compound 107) was obtained in the form of red powder (654 mg, 1.39 mmol, 28%). This red powder was confirmed to be the desired substance (Compound 107) through a comparison in $^1$HNMR spectrum with the reference value. Peak values from $^1$HNMR and $^{13}$CNMR (DMSO-d6) and the measured values of HRMS (ESI) are indicated below.

Compound 107:
$^1$HNMR (DMSO-d6): δ 8.74 (d, J=8.3 Hz, 1H), 8.51 (d, J=7.3 Hz, 1H), 7.94-7.89 (m, 3H), 7.74-7.70 (m, 1H), 7.65 (d, J=8.3 Hz, 1H), 7.55-7.51 (m, 1H), 7.36-7.32 (m, 1H), 7.21 (d, J=7.3 Hz, 1H), 6.83 (s, 1H), 4.47 (t, J=7.1 Hz, 2H), 4.07 (s, 3H), 2.22 (t, J=6.6 Hz, 1H), 1.77-1.63 (m, 4H); $^{13}$CNMR (DMSO-d6, 60° C.) δ 174.6, 158.8, 148.4, 144.5, 139.5, 137.6, 132.7, 127.9, 126.8, 125.5, 124.1, 123.7, 123.6, 122.4, 117.5, 112.6, 107.6, 87.4, 45.6, 42.0, 35.5, 26.2, 22.3;
HRMS (ESI) calcd for $C_{23}H_{23}N_2O_2S$ ([M.Br]$^+$) 391.1480, found 391.1475.

(4) Synthesis of N-hydroxysuccinimidyl ester 109
9.4 mg (20 μmol) of 1-methyl-4-[{3-(4-carboxybutyl)-2 (3H)-benzothiazolylidene}methyl]quinolinium bromide (Compound 107) (FW 471.41), 4.6 mg (40 μmol) of N-hydroxysuccinimide (Compound 108) (FW 115.09), and 7.6 mg (40 μmol) of EDC (1-ethyl-3-(3-dimethylaminopropyl) carbodiimide hydrochloride) (FW 191.70) were stirred in 1 ml of DMF at 25° C. for 16 hours. Thus, N-hydroxysuccinimidyl ester (Compound 109) was obtained, in which the carboxy group of the dye (Compound 107) had been activated. This reaction product was not purified, and the reaction solution (20 mM of a dye) was used for the next reaction without further being treated.

As described above, the compound represented by the chemical formula 5 can be obtained by reacting Compound 109 with the compound obtained by introducing a protecting group to one amino group in tris(2-aminoethyl)amine. More specifically, the compound represented by the chemical formula 5 may be obtained, for example, by causing the above reaction at room temperature in DMF (dimethylformamide) as in the examples to be described below, but the method for obtaining the compound is not limited thereto.

Introduction of a label into the compound of the present invention can be achieved by, for example, reacting the compound without a label introduced thereto (the compound represented by the chemical formula (I) where Z is an atomic group that can form a peptide bond with a labeling compound and does not contain a label) with a labeling compound (for example, a compound represented by the chemical formula 5). More specifically, it can be achieved in the following manner, for example: the labeling compound, an $Na_2CO_3$/$NaHCO_3$ buffer, and water are mixed together, then a DMF solution of the compound without a label introduced thereto is further added and mixed, and the resultant mixture is allowed to stand still at room temperature, thereby causing the above reaction. The introduction of a label also can be achieved by, for example, reacting the compound without a label introduced thereto with the labeling compound in an automated nucleic acid synthesizer. The reaction conditions in the automated nucleic acid synthesizer may be, for example, the same as those for an ordinary reaction to be carried out in an automated nucleic acid synthesizer (for example, polymerization of nucleotides by a phosphoramidite method). Because the compound of the present invention is a cytosine derivative, it can bring about an advantageous effect that, for example, a label can be introduced thereto easily by the reaction in an automated nucleic acid synthesizer. It is to be noted, however, that this effect merely is illustrative and does not limit the present invention by any means.

[Nucleic Acid and Labeling Substance of the Present Invention]

The nucleic acid according to the present invention is, as described above, a nucleic acid including at least one structure represented by the chemical formula (II), a tautomer or stereoisomer thereof, or a salt thereof.

In the chemical formula (II), the main chain length (the number of main chain atoms) of L preferably is an integer of 2 or more. The upper limit thereof is not particularly limited, and is, for example, 100 or less, more preferably 30 or less, and particularly preferably 10 or less.

From the viewpoint of using the nucleic acid of the present invention as a labeling substance or the like, it is preferable that the structure represented by the chemical formula (II) is a structure represented by the following chemical formula (IIa) or (IIb).

In the chemical formulae (IIa) and (IIb), the main chain length (the number of main chain atoms) of each of $L^1$, $L^2$, and $L^3$ preferably is an integer of 2 or more. The upper limit thereof is not particularly limited, and is, for example, 100 or less, more preferably 30 or less, and particularly preferably 10 or less.

$Z^{11}$ and $Z^{12}$ preferably are fluorescent dye moieties that exhibit an exciton effect. With this configuration, a change in environment around the fluorescent dyes upon binding with a target sequence, e.g., increase in fluorescence when a double helix structure is formed, becomes greater, so that the target sequence can be detected more effectively.

In $Z^{11}$ and $Z^{12}$, fluorescent dye moieties that exhibit an exciton effect are not particularly limited. More preferably, $Z^{11}$ and $Z^{12}$ are, for example, each independently a group derived from any one of thiazole orange, oxazole yellow, cyanine, hemicyanine, other cyanine dyes, methyl red, azo dyes, and derivatives thereof. Furthermore, a group derived from any other known dye also can be used as appropriate. Many fluorescent dyes that change the fluorescence intensity by binding to nucleic acids such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and quinoline ring linked to each other with a methine group. It usually exhibits weak fluorescence but gives strong fluorescence emission by intercalating into DNA having a double helix structure. Other examples include dyes such as fluorescein and Cy3.

More preferably, $Z^{11}$ and $Z^{12}$ are each independently a dye moiety represented by any one of the above formulae (7) to (9).

In the formulae (7) to (9), it is more preferable that, in $R^1$ to $R^{21}$, the lower alkyl group is a linear or branched alkyl group with a carbon number of 1 to 6, and the lower alkoxyl group is a linear or branched alkoxyl group with a carbon number of 1 to 6.

In the formulae (7) to (9), it is more preferable that in $R^{11}$ and $R^{12}$, the linking group is a polymethylene carbonyl group with a carbon number of at least 2 and is bound to $L^1$ or $L^2$ in the formula (IIa) or (IIb) in the carbonyl group moiety. The upper limit of the carbon number of the polymethylene carbonyl group is not particularly limited, and is, for example, 100 or less, preferably 50 or less, more preferably 30 or less, and particularly preferably 10 or less.

It is more preferable that the structure represented by the formula (IIa) is a structure represented by the formula (IIa-1) and the structure represented by the formula (IIb) is a structure represented by the formula (IIb-1). In the formulae (IIa-1) and (IIb-1), it is preferable that l, m, and n' are each an integer of 2 or more. The upper limit of each of l, m, and n is not particularly limited, and is, for example, 100 or less, more preferably 30 or less, and particularly preferably 10 or less.

The method for producing the nucleic acid according to the present invention is not particularly limited. For example, the nucleic acid of the present invention can be synthesized (produced) using the compound according to the present invention represented by the chemical formula (I). A specific production method is not particularly limited. For example, the nucleic acid of the present invention may be produced using known synthesis methods (production methods) as appropriate or with reference to such known methods. In order to synthesize the nucleic acid from the compound of the present invention, the synthesis may be carried out, for example, by a known method such as a phosphoramidite method using an automated DNA synthesizer or the like. In order to label the nucleic acid, for example, an NCS group derived from the compound of the present invention represented by the chemical formula (I) may be reacted with a compound having a label. More specifically, for example, a carbonyl group (the chemical formula 1, 1a, 1b, or 1c) activated with an NCS group may be reacted with an amino compound having a label. The label may be, for example, a fluorescent dye moiety (preferably, a fluorescent dye moiety that exhibits an exciton effect), as described above. The step of reacting the NCS with the label may be performed either before or after the polymerization (nucleic acid synthesis). For example, from the viewpoint of preventing a labeled moiety from being damaged in the synthesis step, the label may be introduced after the polymerization (nucleic acid synthesis). However, as in the examples to be described below, the label also may be introduced before the polymerization (nucleic acid synthesis). Because the compound of the present invention represented by the chemical formula (I) is a cytosine derivative, it has an advantageous effect that, for example, even if a label is introduced thereto before polymerization (nucleic acid synthesis), the labeled moiety is less liable to be damaged in the synthesis step. Also, for example, after the compound without a label introduced thereto is reacted with a labeling compound in an automated nucleic acid synthesizer to introduce the label thereto as described above, polymerization (nucleic acid synthesis) may be carried out subsequently in the automated nucleic acid synthesizer. In this manner, introduction of the label and the polymerization (nucleic acid synthesis) can be carried out in the automated nucleic acid synthesizer, i.e., in one container (one pot). This brings about an advantageous effect in that the synthesis can be carried out very easily. The above-described effect can be obtained owing to the fact that the compound of the present invention represented by the chemical formula (I) is a cytosine derivative, which is superior in reactivity, for example. It is to be noted, however, that this effect merely is illustrative, and does not limit the present invention by any means.

As described above, the label is not particularly limited, and any fluorescent dye moiety (dye) or the like can be used. For example, it is preferably a cyanine dye and particularly preferably thiazole orange. The cyanine dye has a chemical structure in which, for example, two heterocycles having hetero atoms are linked to each other with a methine linker. It is possible to synthesize fluorescent dyes with various excitation/emission wavelengths by, for example, changing the kind of the heterocycles or the length of the methine linker, or introducing a substituent into the heterocycles. Furthermore, the introduction of a linker for introducing DNA also is relatively easy. Although thiazole orange hardly emits fluorescence in water, it emits strong fluorescence through an interaction with DNA or RNA. It is considered that, owing to the interaction with the nucleic acid, the interaction between dye molecules is prevented and the rotation around the methine linker located between the two heterocycles of dye molecules is prevented, which leads to an increase in fluorescence intensity. The method of using a thiazole orange dye is well known. It can be used with reference to, for example, H. S. Rye, M. A. Quesada, K. Peck, R. A. Mathies and A. N. Glazer, High-sensitivity two-color detection of double-stranded DNA with a confocal fluorescence gel scanner using ethidium homodimer and thiazole orange, Nucleic Acids Res., 1991, 19, 327-33; and L. G. Lee, C. H. Chen and L. A. Chiu, Thiazole orange: a new dye for reticulocyte analysis, Cytometry, 1986, 7, 508-17.

More specifically, the nucleic acid of the present invention may be produced, for example, by any of synthesis methods described in the following examples, methods equivalent to these synthesis methods, or with reference to these synthesis methods.

A labeling substance synthesized using a nucleic acid derivative of the present invention is a labeling substance produced using the compound of the present invention, a tautomer or stereoisomer thereof, or a salt thereof. Specific examples of the labeling substance include DNA, RNA, and artificial nucleic acids such as PNA (peptide nucleic acid) and LNA (Locked Nucleic Acid). More specific examples of the labeling substance include labeling mononucleotides, labeling oligonucleotides, labeling nucleic acids, and labeling nucleic acid derivatives.

When the labeling substance of the present invention is a labeling nucleic acid, it can be used suitably for nucleic acid detection or amplification checking in the form of a nucleic acid probe or a nucleic acid primer.

EXAMPLES

Examples of the present invention will be described below. The following examples show: a nucleic acid derivative of the present invention; an example of the synthesis of a labeling substance using the nucleic acid derivative; and an example of the use of the labeling substance of the present invention as an exciton oligomer. It is to be noted, however, that the present invention is by no means restricted or limited by the following examples.

Example 1

According to the following Scheme 2, a nucleic acid derivative 4 (the compound of the present invention) represented by the following chemical formula 4 was synthesized from a nucleic acid derivative 2 (the following chemical formula 2).

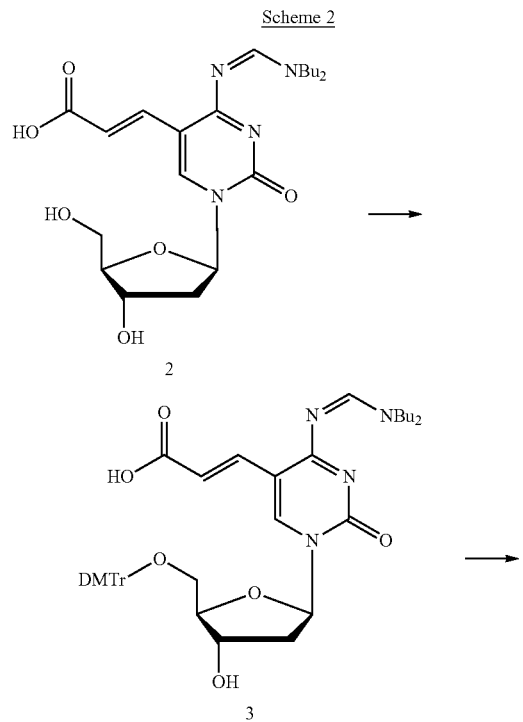

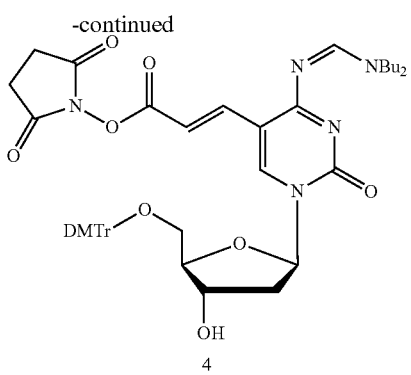

The nucleic acid derivative 2 (formula 2) as a raw material has already been reported (known) (document name: Tetrahedron Letters 2009, 50, 7191). Thus, the nucleic acid derivative 2 was synthesized with reference to the document. As a DNA synthesizer, an H-8 DNA synthesizer (NIHON TECHNO SERVICE CO., LTD.) was used. HPLC was carried out using an LC-20 series (Shimadzu Corporation). MALDI-TOF-MASS was carried out using a Microflex (Bruker Daltonics).

(Synthesis of Nucleic Acid Derivative 3 (Formula 3))

The nucleic acid derivative 2 (1.31 g, 3.0 mmol) was added to a 300 ml Schlenk flask. After nitrogen substitution, 100 ml of dehydrated pyridine and 3.0 g of Molecular sieves 3A were added, and the resultant mixture was stirred for two and a half hours in an ice bath. 4,4'-dimethoxytrityl chloride (1.52 g, 4.50 mmol) and 4-dimethylaminopyridine (0.062 g, 0.51 mmol) were added thereto, and the resultant mixture was stirred at room temperature for 14 hours. After the solvent was vacuum concentrated, the mixture was subjected to purification by silica gel column chromatography (eluent, methanol:methylene chloride=1:10). The solvent was removed by evaporation under reduced pressure, whereby a nucleic acid derivative 3 (formula 3) as the desired substance was obtained in the form of a white solid (1.30 g, yield: 59%). The instrumental analytical values of the nucleic acid derivative 3 (formula 3) are indicated below.

Nucleic acid derivative 3 (formula 3):

$^1$H NMR (270 MHz, CD$_3$OD-d$_4$) δ 8.69 (s, 1H), 8.17 (s, 1H), 7.46-7.11 (m, 10H), 6.80-6.75 (m, 4H), 6.52 (d, J=13.5 Hz, 1H), 6.13 (t, J=8.1 Hz, 1H), 4.32 (m, 1H), 4.11 (m, 1H), 3.70 (s, 6H), 3.58 (t, J=8.1 Hz, 2H), 3.44 (t, J=8.1 Hz, 2H), 3.27 (t, J=5.4 Hz, 2H), 2.56-2.42 (m, 1H), 2.32-2.18 (m, 1H), 1.72-1.58 (m, 4H), 1.42-1.23 (m, 4H), 0.97-0.89 (m, 6H)

(Synthesized of Nucleic Acid Derivative 4 (Formula 4))

The nucleic acid derivative 3 (1.10 g, 3.0 mmol) was added to a 300 ml Schlenk flask. After nitrogen substitution, 200 ml of dehydrated acetonitrile and 4.0 g of Molecular sieves 3A were added, and the resultant mixture was stirred 2 hours in an ice bath. N-hydroxysuccinimide (0.240 g, 2.09 mmol) and 1-ethyl-3-(3-dimethylaminopropyl)carbodiimide hydrochloride (0.432 g, 2.20 mmol) were added thereto, and the resultant mixture was stirred for 22 hours. The reaction solution was filtered, and then was vacuum concentrated. To the residue, 100 ml of methylene chloride and 50 ml of saturated saline were added. 300 ml of the thus-obtained solution was added to a separatory funnel, and the organic layer was washed. After the organic layer was washed 5 times with 50 ml of saturated saline, the organic layer was isolated. Magnesium sulfate was added to the organic layer, which then was allowed to stand still. The magnesium sulfate was filtered out, after which the solvent was removed by evaporation under reduced pressure. Thus, the nucleic acid derivative 4 (formula 4) as the desired substance was obtained in the form of a white solid (1.05 g, yield: 84%). The instrumental analytical values of the nucleic acid derivative 4 (formula 4) are indicated below.

Nucleic acid derivative 4 (formula 4):

$^1$H NMR (270 MHz, CD$_3$OD-d$_4$) δ 8.66 (s, 1H), 8.19 (s, 1H), 7.38 (d, J=13.5 Hz, 1H), 7.28-7.04 (m, 9H), 6.89 (d, J=13.5 Hz, 1H), 6.71-6.67 (m, 4H), 6.05 (t, J=8.1 Hz, 1H), 4.32 (m, 1H), 4.11 (m, 1H), 3.70 (s, 6H), 3.52 (t, J=8.1 Hz, 2H), 3.28 (t, J=8.1 Hz, 2H), 3.18 (t, J=5.4 Hz, 2H), 2.70 (s, 4H), 2.56-2.45 (m, 1H), 2.28-2.18 (m, 1H), 1.65-1.55 (m, 4H), 1.29-1.16 (m, 4H), 0.88-0.79 (m, 6H)

Example 2

Synthesis of Modified DNA Oligomer

In the present example, an H-8 DNA synthesizer (trade name, NIHON TECHNO SERVICE CO., LTD.) was used as a DNA synthesizer, HPLC was carried out using an LC-20 series (trade name, Shimadzu Corporation), and MALDI-TOF-MASS was carried out using a Microflex (trade name, Bruker Daltonics).

First, as a raw material of a modified DNA oligomer, TO$_2$-diamide (the compound represented by the chemical formula 5) was synthesized according to the following Scheme 3.

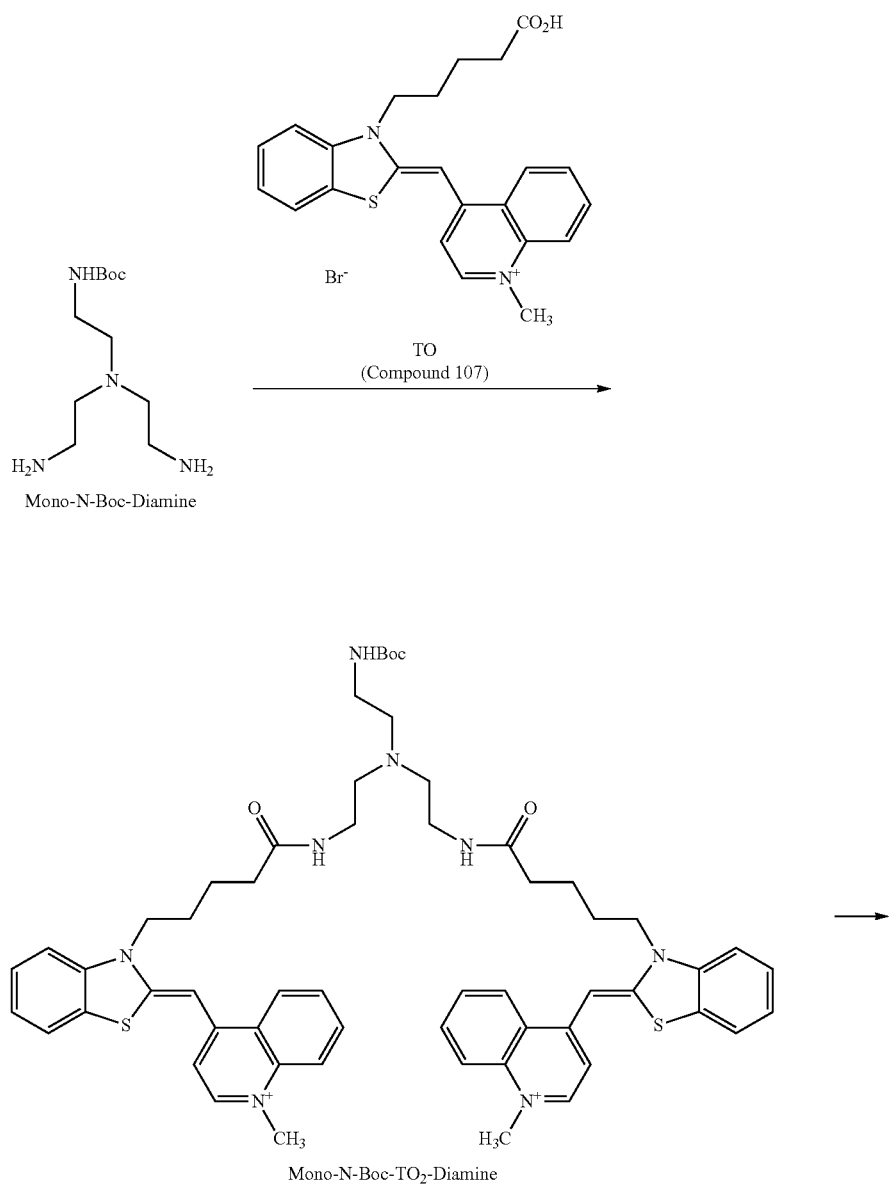

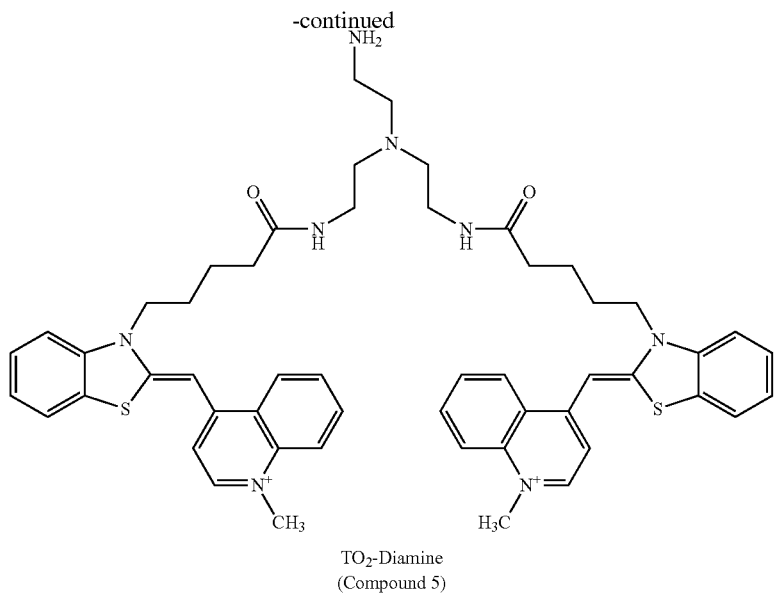

TO₂-Diamine
(Compound 5)

In Scheme 3, Mono-N-Boc-diamine and TO used as raw materials are known compounds. Thus, they were synthesized with reference to methods that have already been reported. It is to be noted here that TO is the same as Compound 107 synthesized according to the above Scheme 1. In Scheme 3, the substituent "Boc" represents a tert-butoxycarbonyl group.

Synthesis of Mono-N-Boc-TO₂-diamide

TO (0.763 g, 1.62 mmol), 7.0 ml of DMF, HOBt (0.243 g, 1.80 mmol), and HBTU (0.521 g, 1.62 mmol) were added to a 50 ml recovery flask. After nitrogen substitution, the mixture was stirred at room temperature for 25 minutes. 3 ml of a DMF solution containing Mono-N-Boc-diamine (0.186 g, 0.755 mmol) was added to this solution, and the resultant mixture was stirred at room temperature for 95 minutes. This solution was added dropwise to 100 ml of ether, and the precipitate produced thereby was collected by centrifugation. This precipitate was purified by reversed-phase (RP-18) flash chromatography (eluent, MeOH:0.1% TFA=50:50 to 60:40, gradient), and the solvent was removed by evaporation under reduced pressure. Thus, Mono-N-Boc-TO₂-diamide as the desired substance was obtained in the form of a red-orange solid (0.584 g, yield: 67%). The instrumental analytical values of the Mono-N-Boc-TO₂-diamide are indicated below.

Mono-N-Boc-TO₂-diamide:

$^1$H NMR (270 MHz, DMSO-$d_6$) δ 8.67 (d, J=8.1 Hz, 2H), 8.56 (d, J=8.1 Hz, 2H), 8.2-7.91 (m, 10H), 7.74-7.65 (m, 4H), 7.55 (t, J=8.1 Hz, 2H), 7.37 (t, J=8.1 Hz, 2H), 7.31 (d, J=8.1 Hz, 2H), 6.84 (s, 2H), 4.61-4.51 (m, 4H), 4.14 (s, 6H), 3.23-3.13 (m, 4H), 2.35-2.24 (m, 4H), 1.85-1.64 (m, 8H), 1.33 (s, 9H);

MS (ESI) m/z 496 (M$^{2+}$), 446 (M$^{2+}$-Boc)

(Synthesis of TO₂-diamide (Compound 5))

Mono-N-Boc-TO₂-diamide (0.220 g, 191 μmol), 3.0 ml of acetonitrile, and 3.0 ml of trifluoroacetic acid were added to a 30 ml recovery flask, and the resultant mixture was stirred at room temperature for 30 minutes. The solvent was removed by evaporation under reduced pressure. Thereafter, 2 ml of triethylamine was added, and further, this was removed by evaporation under reduced pressure. The residue was purified by reversed-phase (RP-18) flash chromatography (eluent, MeOH:0.1% TFA=40:60 to 60:40, gradient), and the solvent was removed by evaporation under reduced pressure. Thus, TO₂-diamide (Compound 5) as the desired substance was obtained in the form of a red-orange solid (0.139 g, yield: 69%). The instrumental analytical values of the TO₂-diamide (Compound 5) are indicated below.

TO₂-diamide (Compound 5):

$^1$H NMR (270 MHz, DMSO-$d_6$) δ 8.67 (d, J=8.1 Hz, 2H), 8.53 (d, J=8.1 Hz, 2H), 8.0-7.80 (m, 10H), 7.72-7.63 (m, 4H), 7.53 (t, J=8.1 Hz, 2H), 7.36 (t, J=8.1 Hz, 2H), 7.27 (d, J=8.1 Hz, 2H), 6.81 (s, 2H), 4.55-4.48 (m, 4H), 4.12 (s, 6H), 3.10-2.95 (m, 4H), 2.35-2.24 (m, 4H), 2.23-2.15 (br, 2H) 1.83-1.66 (m, 8H);

MS (ESI) m/z 446 (M$^{2+}$)

Next, a modified DNA oligomer (the nucleic acid of the present invention) was synthesized by a conventional amidite method. More specifically, first, NHS-Carboxy-dC was introduced to the desired position as described in Example 1 (the chemical formula 4), and immediately after the introduction, the TO₂-diamide (the chemical formula 5) was reacted in the automated DNA synthesizer. The reaction between Compounds 4 and 5 in the automated DNA synthesizer was caused under the same reaction conditions as those for an ordinary reaction to be carried out in an automated DNA synthesizer (i.e., polymerization of nucleotides by an amidite method). The reaction in the automated DNA synthesizer was allowed to proceed, whereby nucleotides were polymerized to synthesize an oligonucleotide. The thus-obtained oligonucleotide was cut out from CPG and deprotected in 28% ammonia water at 55° C. for 4 hours. The oligonucleotide was purified by HPLC equipped with a reversed-phase (R-18) column. The target sequence (SEQ ID NO: 1 shown below) was confirmed by MALDI-TOF-MASS. The measurement results are as follows.

(SEQ ID NO: 1)
5'-GAGTGCcTTGACGATAC-3',

Calcd. 6156.61, Obs. 6158.3

In the sequence of the above SEQ ID NO: 1, "c (the lower-case alphabetic character c)" indicates a labeled cytosine derivative, which is represented by the following chemical formula 1000.

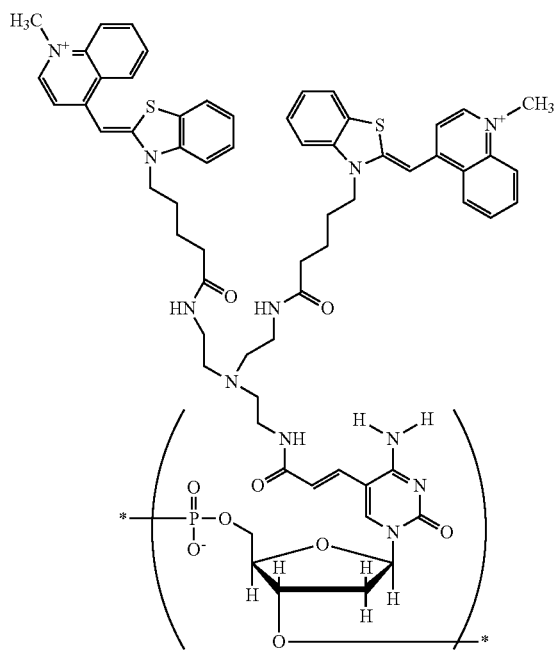

Example 3

Performance of Modified DNA Oligomer in Isothermal Nucleic Acid Amplification Method In a SmartAmp method (NATURE METHODS (2007), VOL. 4, NO. 3, p 257, Japanese Patent No. 3897805), which is a known isothermal nucleic acid amplification method, the performance of a DNA oligomer in which a thymine base was modified with a fluorescent dye (SEQ ID NO: 2 shown below) was compared with the performance of the DNA oligomer in which a cytidine base was modified with a fluorescent dye (SEQ ID NO: 1 shown above) (see FIG. 1). SEQ ID NO: 2 is the same as SEQ ID NO: 1, except that, instead of the cytidine base, the thymine base was modified with the fluorescent dye. In SEQ ID NO: 2, the lower-case letter "t" indicates the thymine base modified with the fluorescent dye. The thymine base modified with the fluorescent dye is represented by the following chemical formula 110.

5'-GAGTGCCTtGACGATAC-3' (SEQ ID NO: 2)

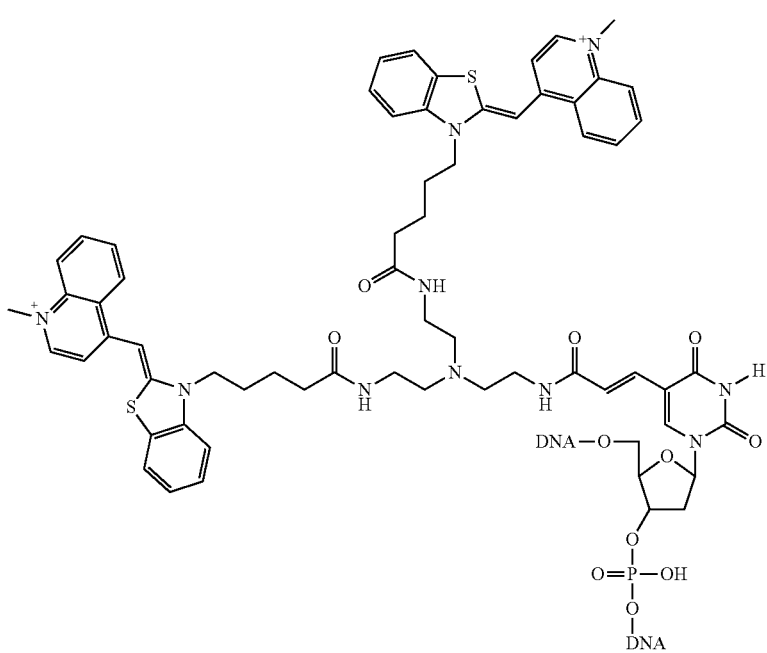

FIG. 1 shows the result of the nucleic acid amplification by the above-described SmartAmp method. As can be seen from FIG. 1, in either of the case where the DNA oligomer in which the thymine base was modified with the fluorescent dye (SEQ ID NO: 2) was used and the case where the DNA oligomer in which the cytidine base was modified with the fluorescent dye (SEQ ID NO: 1) was used, signals indicating amplification were observed in about 16 minutes. This demonstrates that their performances are substantially equivalent.

INDUSTRIAL APPLICABILITY

As specifically described above, the compound of the present invention is not a thymine derivative but a cytosine derivative. Thus, the compound of the present invention can be used as a reagent, other than thymine derivatives, for synthesizing nucleic acids (such as DNA and RNA, for example), so that it can alleviate the restrictions on the sequence design of modified nucleic acid (such as DNA and RNA, for example) oligomers. Furthermore, according to the present invention, it is also possible to provide a nucleic acid and labeling substance that can be produced using the compound of the present invention and a detection method using the labeling substance. Moreover, the use of the compound of the present invention is not limited to those described above, and the compound of the present invention is applicable to a broad range of uses.

SEQUENCE LISTING

TF13033WO sequence list 2013.08.30_ST25_ST25.txt

The invention claimed is:
1. A compound represented by the following chemical formula 1a or (Ia-1); a tautomer of the compound; or a salt of the compound, or the tautomer:

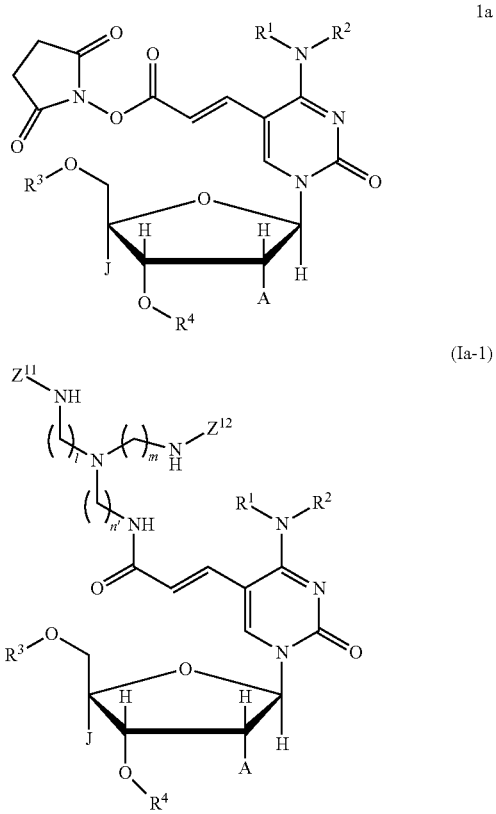

```
                        SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: origomer
<220> FEATURE:
<221> NAME/KEY: misc_feature
<222> LOCATION: (7)..(7)
<223> OTHER INFORMATION: n represents cytosine introduced fluorescent dye

<400> SEQUENCE: 1
gagtgcnttg acgatac                                                  17

<210> SEQ ID NO 2
<211> LENGTH: 17
<212> TYPE: DNA
<213> ORGANISM: Artificial Sequence
<220> FEATURE:
<223> OTHER INFORMATION: origomer
<220> FEATURE:
<221> NAME/KEY: misc_feature
<222> LOCATION: (9)..(9)
<223> OTHER INFORMATION: n represents thymine introduced fluorescent dye

<400> SEQUENCE: 2
gagtgcctng acgatac                                                  17
``` where in the chemical formulas 1a and (Ia-1),
- $R^1$ and $R^2$ are each a hydrogen or a protecting group of an amino group and may be identical to or different from each other, or alternatively, $R^1$ and $R^2$ together may form a protecting group of an amino group, with the proviso that one of these substituents is always an acyl-type amine protecting group,
- $R^3$ is a protecting group of a hydroxy group,
- $R^4$ is —P(NR$^5$R$^6$)(OR$^7$) ($R^5$ and $R^6$ are each an alkyl group and may be identical to or different from each other, $R^7$ is a protecting group of a hydroxy group),
- J is a hydrogen atom or an alkoxy group,
- A is a hydrogen atom, a protected hydroxyl group, an alkyl group, an aralkyl group, an alkoxy group, a halogen, a trifluoromethyl group, a fluoroalkyl group, a trisubstituted silyl group, or a protected thiol group,
- or alternatively, J and A when bonded together may form a bridging linkage wherein J is $CH_2$, O, or S, A is $CH_2$, O, or S and J and A may be identical to or different from each other,
- 1, m, and n' are each an integer of 2 to 100, 1, m, and n' may be identical to or different from each other, $Z^{11}$ and $Z^{12}$ are each a fluorescent dye moiety that exhibits an exciton effect.

2. The compound according to claim 1, wherein, in A in the chemical formulas 1a and (Ia-1), the alkyl group is a methyl group, an ethyl group, a propyl group, a butyl group, a pentyl group, or a hexyl group, and the aralkyl group is a benzyl group, the alkoxy group is a methoxy group,
   a tautomer of the compound; or
   a salt of the compound, or the tautomer.

3. The compound according to claim 1, wherein the structure represented by the chemical formula 1a is a structure represented by the following chemical formula 1:

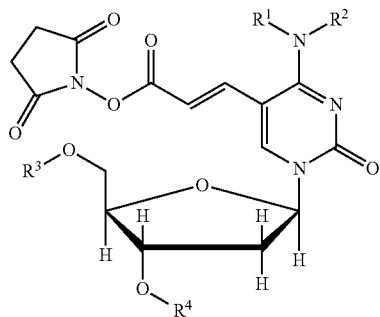

where in the chemical formula 1, $R^1$, $R^2$, $R^3$, and $R^4$ are identical to those in the chemical formula 1a;
   a tautomer of the compound; or
   a salt of the compound, or the tautomer.

4. The compound according to claim 1, wherein, in the formula (Ia-1), $Z^{11}$ and $Z^{12}$ are each independently a substituent group derived from a dye selected from the group consisting of thiazole orange, oxazole yellow, cyanine, hemicyanine, Cy5, methyl red, azo dyes, and biotin;
   a tautomer of the compound; or
   a salt of the compound, or the tautomer.

5. The compound according to claim 1, wherein, in the formula (Ia-1),
$Z^{11}$ and $Z^{12}$ are each independently a substituent group represented by any one of the following formulae (7) to (9) and includes a counter anion:

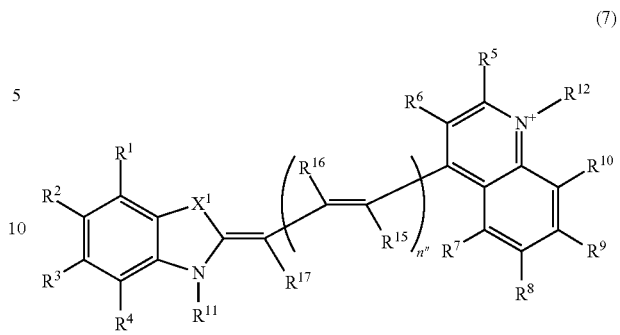

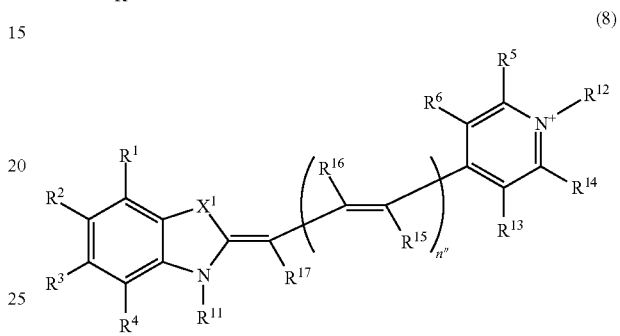

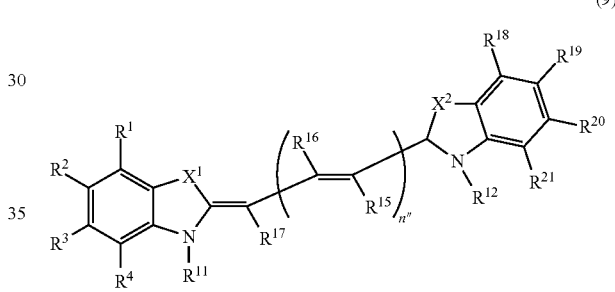

where in the formulae (7) to (9),
- $X^1$ and $X^2$ are S, O, or Se,
- each of n" and n is 0 or 1,
- $R^1$ to $R^{10}$ and $R^{13}$ to $R^{21}$ are each independently a hydrogen atom, a halogen atom, a lower alkyl group, a lower alkoxyl group, a nitro group, or an acyl-protecting group protected amino group,
- one of $R^{11}$ and $R^{12}$ is —(CH$_2$)$_n$—CO—, wherein n is 2 to 100, and in —(CH$_2$)—CO—, the carbonyl group (CO) is bound to NH in the chemical formula (Ia-1), and the other is a hydrogen atom or a lower alkyl group,
- $R^{15}$ and $R^{16}$ are hydrogen atoms,
- $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively;
   a tautomer of the compound; or
   a salt of the compound, or the tautomer.

6. The compound according to claim 5, wherein, in $R^1$ to $R^{21}$ in the formulae (7) to (9), the lower alkyl group is a linear or branched alkyl group with a carbon number of 1 to 6, and the lower alkoxyl group is a linear or branched alkoxyl group with a carbon number of 1 to 6;
   a tautomer of the compound; or
   a salt of the compound, or the tautomer.

7. The compound according to claim 5, wherein, in $R^{11}$ and $R^{12}$ in the formulae (7) to (9), the linking group is —(CH$_2$)$_n$—CO—, wherein n is 2 to 100, and in —$(CH_2)_n$—CO—, the carbonyl group (CO) is bound to NH in the chemical formula (Ia-1);
a tautomer of the compound; or
a salt of the compound, or the tautomer.

8. The compound according to claim 5, wherein, in the formula (Ia-1),
$Z^{11}$ and $Z^{12}$ are each independently a substituent group represented by the formula (7) or (8), and
$Z^{11}$ and $Z^{12}$ represented by the formula (7) or (8) is a group represented by the following formula (19) or (20) and includes a counter anion:

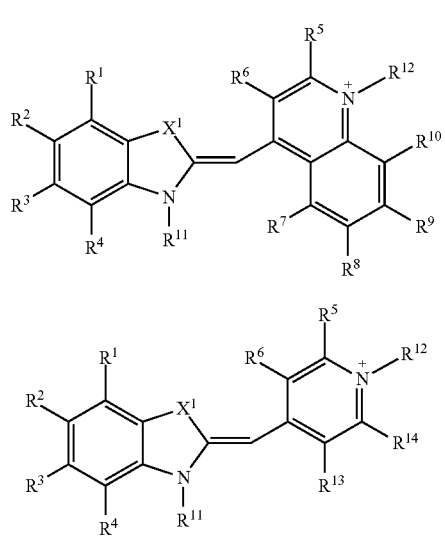

where in the formulae (19) and (20),
$X^1$ $R^1$ to $R^{10}$, $R^{13}$ and $R^{14}$, and $R^{11}$ and R are identical to those in the formulae (7) to (9);
a tautomer of the compound; or
a salt of the compound, or the tautomer.

9. The compound according to claim 8, wherein
$Z^{11}$ and $Z^{12}$ are each independently a substituent group represented by the above formula (19),
where in the formula (19),
$X^1$ is S,
$R^1$ to $R^{10}$ are hydrogen atoms, and
one of $R^{11}$ and $R^{12}$ is —$(CH_2)_n$—CO—, wherein n is 2 to 100, and in —$(CH_2)_n$—CO—, the carbonyl group (CO) is bound to NH in the chemical formula (Ia-1), and the other is a methyl group;
a tautomer of the compound; or
a salt of the compound, or the tautomer.

10. The compound according to claim 8, wherein, in the formula (Ia-1),
$Z^{11}$ and $Z^{12}$ are each independently a substituent group represented by the above formula (19),
where in the formula (19),
$X^1$ is S,
$R^1$, $R^4$, $R^5$, $R^6$, $R^7$, $R^9$, and $R^{10}$ are hydrogen atoms,
$R^2$, $R^3$, and $R^{12}$ are methyl groups,
$R^8$ is a halogen atom, and
$R^{11}$ is —$(CH_2)_n$—CO—, wherein n is 2 to 100, and in —$(CH_2)_n$—CO—, the carbonyl group (CO) is bound to NH in the chemical formula (Ia-1);
a tautomer of the compound; or
a salt of the compound, or the tautomer.

11. The compound according to claim 5, wherein, in the formula (Ia-1),
$Z^{11}$ and $Z^{12}$ are each independently a substituent group represented by the above formula (7),
where in the formula (7),
$X^1$ is S,
n" is 1,
$R^1$ to $R^{10}$, $R^{15}$, $R^{16}$, and $R^{17}$ are hydrogen atoms,
$R^{11}$ is —$(CH_2)_n$—CO—, wherein n is 2 to 100, and in —$(CH_2)_n$—Co—, the carbonyl group (CO) is bound to NH in the chemical formula (Ia-1), and
$R^{12}$ is a methyl group;
a tautomer of the compound; or
a salt of the compound, or the tautomer.

12. The compound according to claim 1, wherein, in the formula (Ia-1),
$Z^{11}$ and $Z^{12}$ are each independently a substituent group represented by any one of the following formulae:

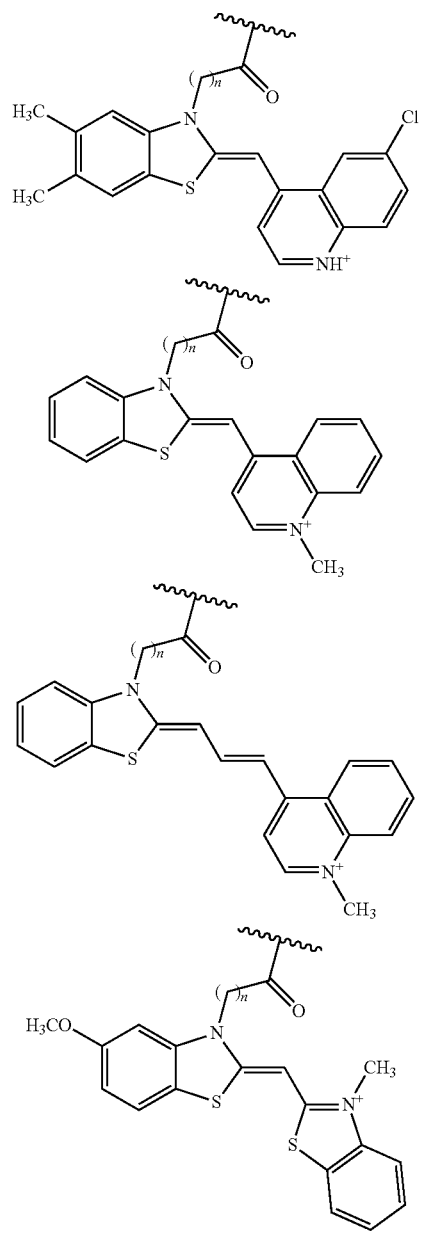

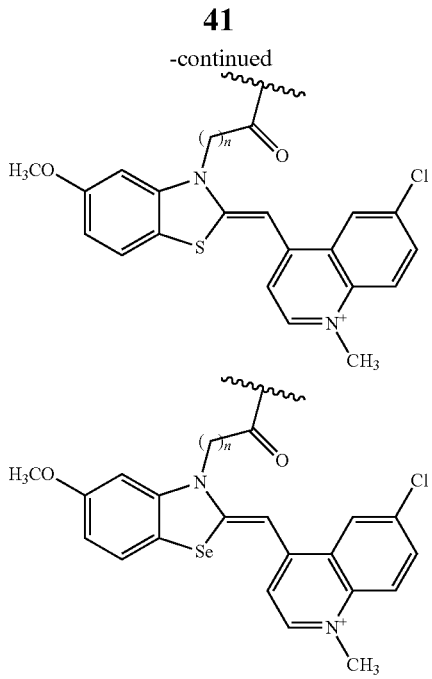

where in each of the above chemical formulae, a wavy line indicates a position at which the atomic group is bound to $L^1$ or $L^2$, and n is 2 to 6;

a tautomer of the compound; or a salt of the compound, or the tautomer.

13. The compound according to claim 1, wherein, in the formula (Ia-1), $Z^{11}$ and $Z^{12}$ are each independently a substituent group represented by any one of the following formulae:

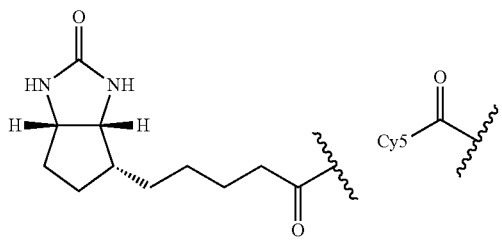

where in each of the above chemical formulae, a wavy line indicates a position at which the atomic group is bound to NH, and Cy5 is a group derived from the cyanine dye Cy5;

a tautomer of the compound; or a salt of the compound, or the tautomer.

14. A nucleic acid comprising at least one structure represented by the following chemical formula 1b-2 or (Ia-2):

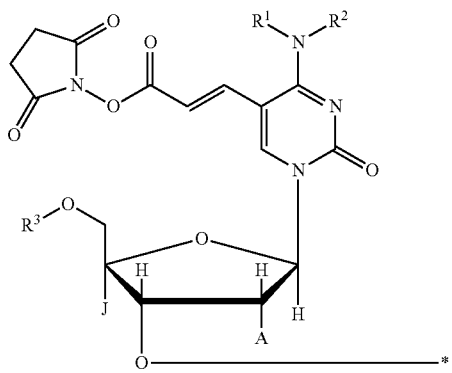

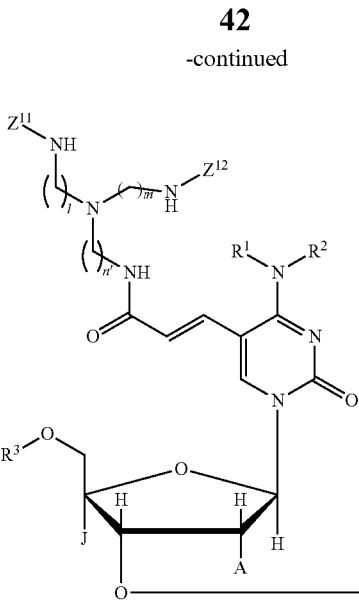

where in the chemical formulas 1b-2 and (Ia-2), $R^1$ and $R^2$ are each a hydrogen or a protecting group of an amino group and may be identical to or different from each other, or alternatively, $R^1$ and $R^2$ together may form a protecting group of an amino group, with the proviso that one of these substituents is always an acyl-type amine protecting group, $R^3$ is a protecting group of a hydroxy group, J is a hydrogen atom, an alkyl group, or an alkoxy group, A is a hydrogen atom, a protected hydroxyl group, an alkyl group, an aralkyl group, an alkoxy group, a halogen, a trifluoromethyl group, a fluoroalkyl group, a trisubstituted silyl group, or a protected thiol group, or alternatively, J and A when bonded together may form a bridging linkage wherein J is $CH_2$, O, or S, A is $CH_2$, O, or S and J and A may be identical to or different from each other, 1, m, and n' are each an integer of 2 to 100, 1, m, and n' may be identical to or different from each other, $Z^{11}$ and $Z^{12}$ are each a fluorescent dye moiety that exhibits an exciton effect, and the mark "*" indicates a position at which the structure is bonded to a terminal $PO_3^{31}$ group of a nucleic acid;

a tautomer of the compound; or a salt of the compound, or the tautomer.

15. The nucleic acid according to claim 14, represented by the following chemical formula 1001 and includes a counter anion:

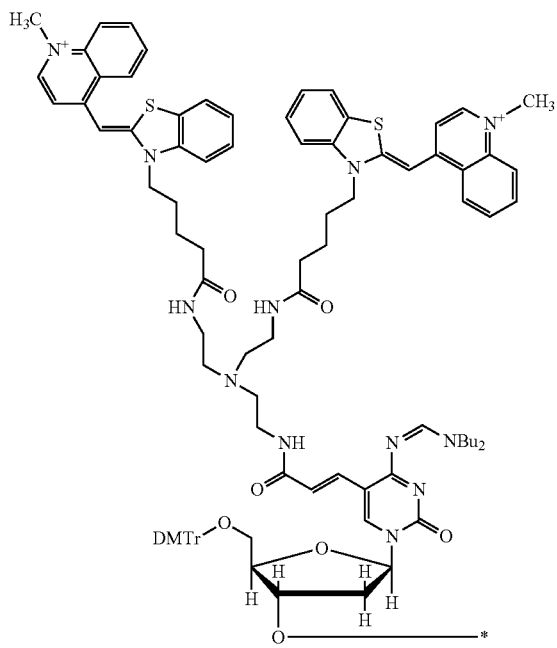

where in the chemical formula 1001, the mark "*" is identical to that in the chemical formula (Ia-2);
  a tautomer of the compound; or
  a salt of the compound, or the tautomer.

16. A nucleic acid comprising at least one structure represented by the following chemical formula (IIa-1) and includes a counter cation:

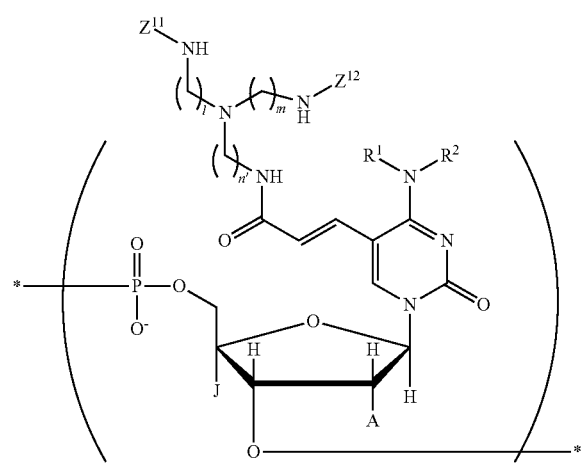

(IIa-1)

where in the chemical formula (IIa-1),

R$^1$ and R$^2$ are each a hydrogen or a protecting group of an amino group and may be identical to or different from each other, or alternatively, R$^1$ and R$^2$ together may form a protecting group of an amino group, with the proviso that one of these substituents is always an acyl-type amine protecting group, J is a hydrogen atom an alkyl group, or an alkoxy group, A is a protected hydroxyl group, an alkyl group, an aralkyl group, an alkoxy group, a halogen, a trifluoromethyl group, a fluoroalkyl group, a trisubstituted silyl group, or a protected thiol group, or alternatively, J and A when bonded together may form a bridging linkage wherein J is CH$_2$, O, or S, A is CH$_2$, O, or S and J and A may be identical to or different from each other, l, m, and n' are each an integer of 2 to 100, l, m, and n' may be identical to or different from each other, Z$^{11}$ and Z$^{12}$ are each a fluorescent dye moiety that exhibits an exciton effect, and the mark "*" indicates a position at which the structure is bound to another atom or atomic group, and at least one O atom in a phosphoric acid linkage may be substituted with an S atom;

a tautomer of the compound; or a salt of the compound, or the tautomer.

17. A nucleic acid comprising at least one structure represented by the following chemical formula 1b and includes one counter cation:

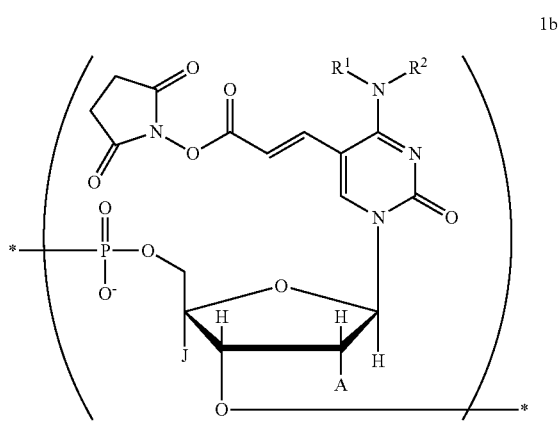

1b where in the chemical formula 1b,

R$^1$ and R$^2$ are each a hydrogen or a protecting group of an amino group and may be identical to or different from each other, or alternatively, R$^1$ and R$^2$ together may form a protecting group of an amino group, with the proviso that one of these substituents is always an acyl-type amine protecting group, J is a hydrogen atom, an alkyl group, or an alkoxy group, A is a hydrogen atom, a protected hydroxyl group, an alkyl group, an aralkyl group, an alkoxy group, a halogen, a trifluoromethyl group, a fluoroalkyl group, a trisubstituted silyl group, or a protected thiol group, or alternatively, J and A when bonded together may form a bridging linkage wherein J is CH$_2$, O, or S, A is CH$_2$, O, or S and J and A may be identical to or different from each other, and at least one O atom in a phosphoric acid linkage may be substituted with an S atom;

a tautomer of the compound; or a salt of the compound, or the tautomer.

18. A nucleic acid comprising at least one structure represented by the following chemical formula 1c and includes one counter cation:

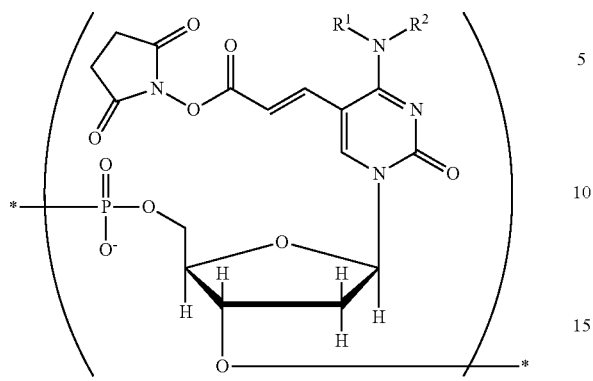

where in the chemical formula 1c,
R$^1$ and R$^2$ are each a hydrogen or a protecting group of an amino group and may be identical to or different from each other, or alternatively, R$^1$ and R$^2$ together may form a protecting group of an amino group, with the proviso that one of these substituents is always an acyl-type amine protecting group, and
at least one O atom in a phosphoric acid linkage may be substituted with an S atom;
a tautomer of the compound; or
a salt of the compound, or the tautomer.

* * * * *